(12) United States Patent
Landman et al.

(10) Patent No.: US 9,216,295 B2
(45) Date of Patent: Dec. 22, 2015

(54) CARDIAC RESYNCHRONIZATION THERAPY LOSS DIAGNOSTICS

(75) Inventors: Sean R. Landman, Minneapolis, MN (US); Robert W. Stadler, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 887 days.

(21) Appl. No.: 13/297,104

(22) Filed: Nov. 15, 2011

(65) Prior Publication Data

US 2013/0110191 A1    May 2, 2013

Related U.S. Application Data

(60) Provisional application No. 61/553,716, filed on Oct. 31, 2011.

(51) Int. Cl.
*A61N 1/362* (2006.01)
*A61N 1/372* (2006.01)
*A61N 1/368* (2006.01)

(52) U.S. Cl.
CPC .......... *A61N 1/37282* (2013.01); *A61N 1/3627* (2013.01); *A61N 1/3622* (2013.01); *A61N 1/3682* (2013.01); *A61N 1/37235* (2013.01)

(58) Field of Classification Search
USPC ....................................................... 600/513
See application file for complete search history.

(56) References Cited

U.S. PATENT DOCUMENTS

| | | | |
|---|---|---|---|
| 6,907,289 | B2 | 6/2005 | Stahmann et al. |
| 2005/0137629 | A1 | 6/2005 | Dyjach et al. |
| 2011/0022981 | A1 | 1/2011 | Mahajan et al. |
| 2011/0105860 | A1* | 5/2011 | Houben et al. ................. 600/301 |

FOREIGN PATENT DOCUMENTS

WO   2011053723 A1   5/2011

OTHER PUBLICATIONS

Ousdigian et al.. "Reduced Bi-Ventricular Pacing is Associated with Decreased Survival in 10,830 CRT-D Patients with AF," PowerPoint Presentation, May 13, 2010, 14 pp.
Koplan et al., "Heart Failure Decompensation and All-Cause Mortality in Relation to Percent Biventricular Pacing in Patients with Heart Failure," Journal of the American College of Cardiology, vol. 53, No. 4, Jan. 27, 2009, pp. 355-360.
Hayes et al., "Cardiac resynchronization therapy and the relationship of percent biventricular pacing to symptoms and survival," Heart Rhythm, vol. 8, No. 9, pp. 1469-1475, Sep. 2011.
Borek et al., "Impact of AF on Mortality in 51,058 Patents with CRT-D," PowerPoint Presentation, May 13, 2010, 18 pp.

(Continued)

*Primary Examiner* — Carl H Layno
*Assistant Examiner* — Jon Eric C Morales
(74) *Attorney, Agent, or Firm* — Michael C. Soldner

(57) ABSTRACT

In some examples, an IMD provides CRT data that indicates an amount of time that CRT was not delivered by the IMD, such as the % CRT. In some examples, a CRT loss diagnosis module apportions the amount of time that CRT was not delivered amongst predetermined reasons for loss of CRT based on the CRT data and sensed cardiac data from the IMD. An external computing device may present a representation of the apportionment to a user, e.g., a clinician. The external computing device may also analyze the apportionment, and recommend programming changes for the delivery of CRT by the IMD based on the analysis.

12 Claims, 12 Drawing Sheets

(56) References Cited

OTHER PUBLICATIONS

U.S. Appl. No. 13/316,177, by Helen W. Otto, filed Dec. 9, 2011.
Office Action from U.S. Appl. No. 13/316,177, dated Mar. 7, 2014, 5 pp.
(PCT/US2012/62052) PCT Notification of Transmittal of the International Search Report and the Written Opinion of the International Searching Authority.
Response to Office Action dated Mar. 7, 2014, from U.S. Appl. No. 13/316,177, filed May 28, 2014, 12 pp.
Notice of Allowance from U.S. Appl. No. 13/316,177, dated Jun. 12, 2014, 5 pp.
Notice of Allowance from U.S. Appl. No. 13/316,177, dated Aug. 13, 2014, 4 pp.

* cited by examiner

CARDIAC RESYNCHRONIZATION THERAPY LOSS DIAGNOSTICS

This application claims the benefit of U.S. Provisional Patent Application No. 61/553,716, filed Oct. 31, 2011, the entire content of which is incorporated herein by reference.

TECHNICAL FIELD

The disclosure relates to implantable medical devices, and, more particularly, to implantable medical devices configured to deliver cardiac stimulation therapy.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device (IMD) may sense intrinsic depolarizations of the heart, and control the delivery of therapeutic stimulation to the heart based on the sensing.

Cardiac resynchronization therapy (CRT) is one type of therapy delivered by an IMD. CRT may help enhance cardiac output by resynchronizing the electromechanical activity of the ventricles of the heart. Ventricular dysynchrony may occur in patients that suffer from congestive heart failure (CHF). In some examples, CRT involves delivery of pacing pulses to both ventricles ("biventricular pacing") to synchronize their contraction. In other examples, CRT involves delivery of pacing pulses to one ventricle to synchronize its contraction with that of the other ventricle, such as pacing the left ventricle to synchronize its contraction with that of the right ventricle.

In general, it is believed that the benefit of CRT depends on consistent delivery of CRT, e.g., depends on CRT being delivered essentially constantly. Some existing IMDs track the amount of time CRT was or was not delivered. Based on such data, an external programmer in communication with the IMD may provide a value of a diagnostic metric to a user. An example of a diagnostic metric for evaluating CRT is the percent of a period time, e.g., since the last interrogation of the implantable medical device, that the IMD has delivered (or not delivered) CRT to the user. This metric has been referred to as % CRT.

SUMMARY

Existing CRT diagnostics provided by IMDs and IMD programmers illustrate the extent to which CRT is being delivered by an implantable medical device. However, to the extent CRT is not delivered at or near 100% of the time, it may be desired to understand the reason or reasons for the loss of CRT. Understanding the reasons for loss of CRT may allow a clinician to take corrective action, e.g., change one or more programmable parameters that control the delivery of CRT by the IMD to increase the delivery of CRT.

In general, techniques for determining and indicating reasons for loss of CRT are described. More particularly, techniques for illustrating the relative impact of various predetermined possible reasons for loss of CRT are described. Based on the relative impact of the various reasons, a clinician may more easily determine what programming changes to make for the delivery of CRT by the IMD.

In some examples, an IMD provides CRT data that indicates an amount of time that CRT was not delivered by the IMD, such as a percentage of the time since the last download of data from the IMD that CRT was or was not delivered. In some examples, a CRT loss diagnosis module apportions the amount of time that CRT was not delivered to the predetermined reasons for loss of CRT based on the CRT data and sensed cardiac data from the IMD. An external computing device may present a representation of the apportionment to a user, e.g., a clinician. The external computing device may also analyze the apportionment, and recommend programming changes for the delivery of CRT by the IMD based on the analysis.

In one example, a system comprises a processor and a CRT loss diagnosis module. The processor is configured to receive data generated by an implantable medical device (IMD) that is configured to deliver cardiac resynchronization therapy (CRT), wherein the received data comprises CRT data and sensed cardiac data, wherein the CRT data indicates an amount of time for which the IMD did not deliver CRT to a patient, and wherein the sensed cardiac data indicates intrinsic cardiac activity of the patient that was sensed by the IMD. The CRT loss diagnosis module is configured to analyze the CRT data and the sensed cardiac data, and apportion the amount of time amongst a plurality of predetermined reasons for CRT loss based on the analysis.

In another example, a method comprises receiving data generated by an implantable medical device (IMD) that is configured to deliver cardiac resynchronization therapy (CRT), wherein the received data comprises CRT data and sensed cardiac data, wherein the CRT data indicates an amount of time for which the IMD did not deliver CRT to a patient, and wherein the sensed cardiac data indicates intrinsic cardiac activity of the patient that was sensed by the IMD. The method further comprises analyzing, by a CRT loss diagnosis module, the CRT data and the sensed cardiac data, and apportioning, by a CRT loss diagnosis module, the amount of time amongst a plurality of predetermined reasons for CRT loss based on the analysis.

In another example a computer-readable storage medium comprises instructions that cause a processor to receive data generated by an implantable medical device (IMD) that is configured to deliver cardiac resynchronization therapy (CRT), wherein the received data comprises CRT data and sensed cardiac data, wherein the CRT data indicates an amount of time for which the IMD did not deliver CRT to a patient, and wherein the sensed cardiac data indicates intrinsic cardiac activity of the patient that was sensed by the IMD. The instructions further cause the processor to analyze the CRT data and the sensed cardiac data, and apportion the amount of time amongst a plurality of predetermined reasons for CRT loss based on the analysis.

The details of one or more examples are set forth in the accompanying drawings and the description below. Other features, objects, and advantages will be apparent from the description and drawings, and from the claims.

DETAILED DESCRIPTION

Figure 1:
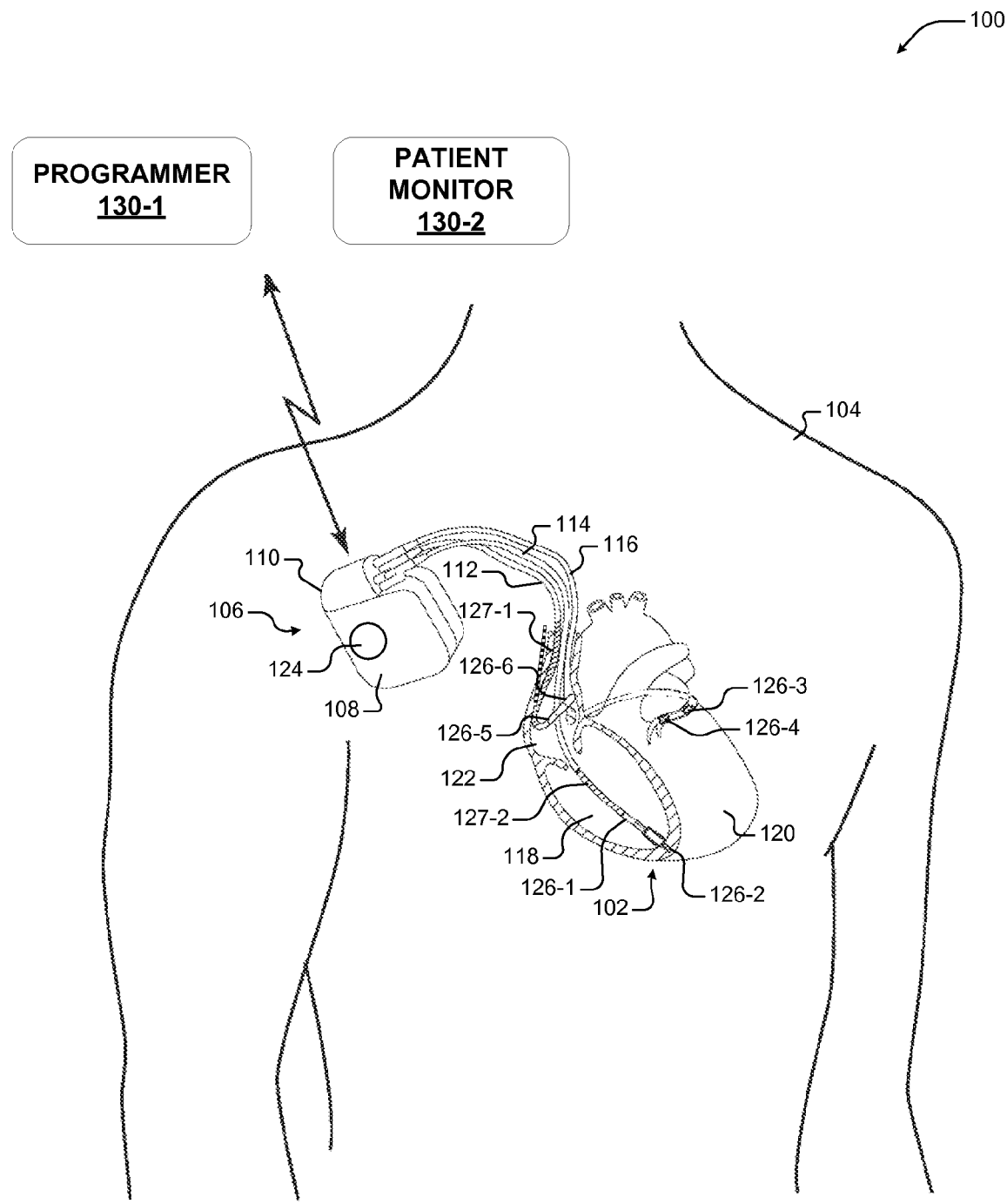
FIG. 1 is a conceptual diagram illustrating an example system that includes an IMD that delivers CRT.

FIG. 1 is a conceptual diagram illustrating an example system 100 that includes an IMD 106 that delivers CRT to a patient 104 and, more particularly, to a heart 102 of the patient. As described herein, system 100 may be used in the implementation of techniques for illustrating CRT performance. More particularly, system 100 may be used in the implementation of techniques for tracking the amount of time CRT is not delivered to the patient, and apportioning such time amongst a plurality of predetermined reasons or causes for loss of CRT to illustrate the reasons or causes for impaired CRT performance.

In the illustrated example, IMD 106 is coupled to leads 112, 114, and 116. IMD 106 may be, for example, an implantable pacemaker, cardioverter, and/or defibrillator that provide electrical signals to heart 102 using one or more of leads 112, 114, and 116. Leads 112, 114, and 116 extend into heart 102 of patient 104. Leads 112, 114, and 116 sense electrical activity of heart 102 and/or deliver electrical stimulation to heart 102. Right ventricular (RV) lead 114 extends into right ventricle 118 of heart 102 through one or more veins (not shown), the superior vena cava (not shown), and right atrium 122. Left ventricular (LV) coronary sinus lead 116 extends through one or more veins, the vena cava, right atrium 122, and into the coronary sinus to a region adjacent to the free wall of left ventricle 120 of heart 102. Right atrial (RA) lead 112 extends into right atrium 122 of heart 102 through one or more veins and the vena cava.

IMD 106 includes a housing 108 and a connector block 110. Leads 112, 114, and 116 are mechanically and electrically coupled to IMD 106 via connector block 110. Housing 108 may enclose a signal generator that generates therapeutic stimulation, such as cardiac pacing pulses and defibrillation pulses, as well as a sensing module for monitoring the rhythm of heart 12. In such examples, leads 112, 114, and 116 may be coupled to the signal generator and sensing module of IMD 106 via connector block 110. IMD 106 may sense electrical signals attendant to the depolarization and repolarization of heart 102 via leads 112, 114, and 116. IMD 106 may also provide electrical stimulation to heart 102 via leads 112, 114, and 116.

IMD 106 may provide pacing pulses to heart 102 based on the electrical signals sensed within heart 102. In some examples, IMD 106 may provide pacing pulses in a manner that provides CRT to heart 102. In some examples, the LV lead 116 may be used in combination with the RV lead 114 to deliver biventricular pacing to the heart, which may provide CRT to the patient. CRT may be used to treat heart failure-inducted conduction disturbances and/or ventricular dysynchrony. In some cases, CRT may help restore the mechanical sequence of ventricular activation and contraction. In some examples, CRT may involve biventricular pacing, e.g., via the RV lead and LV lead, to synchronize the contraction of both ventricles. In other examples, CRT may involve pacing one of the ventricles, e.g., the LV via the LV lead, to synchronize its contraction with that of the other ventricle.

IMD 106 may also provide defibrillation and/or cardioversion therapy to heart 102. For example, IMD 106 may detect tachyarrhythmia of heart 102, such as fibrillation of the ventricles 118 and 120, and deliver cardioversion or defibrillation therapy to heart 102 in the form of electrical pulses. In some implementations, IMD 106 may be programmed to deliver a progression of therapies, e.g., pulses with increasing energy levels, until a tachyarrhythmia of heart 102 is stopped. IMD 106 may detect tachycardia or fibrillation employing one or more tachycardia or fibrillation detection techniques known in the art.

Leads 112, 114, and 116 include electrodes 126 and 127. IMD 106 may sense electrical signals via electrodes 126 and 127. IMD 106 may also provide electrical signals, e.g., stimulation, to heart 102 using electrodes 126 and 127. The illustrated type, location and number of electrodes on leads 112, 114, and 116 are merely an example, and other types, numbers and locations are contemplated.

Bipolar electrodes 126-1 and 126-2 are located adjacent to the distal end of lead 114 in right ventricle 118. Bipolar electrodes 126-3 and 126-4 are located adjacent to the distal end of lead 116 in the coronary sinus adjacent to left ventricle 120. Bipolar electrodes 126-5 and 126-6 are located adjacent to the distal end of lead 112 in right atrium 122. There are no electrodes located in the left atrium in the illustrated example. However, other examples may include electrodes in or adjacent left atrium.

Electrodes 126-1, 126-3, 126-4, and 126-5 may take the form of ring electrodes. Electrodes 126-2 and 126-6 may take the form of tip electrodes, e.g., extendable helix tip electrodes mounted retractably within insulative electrode heads that facilitate fixation of leads to the myocardium. Leads 112 and 114 may also include elongated electrodes 127-1 and 127-2, respectively, which may take the form of a coil.

IMD 106 includes a housing electrode 124, which may be formed integrally with an outer surface of the hermetically-sealed housing 108 of IMD 106, or otherwise coupled to housing 106. Although a single housing electrode 124 is illustrated in FIG. 1, IMD 106 may include more or less than a single housing electrode 124.

IMD 106 may sense electrical signals attendant to the depolarization and repolarization of heart 12 via electrodes 124, 126 and 127. The electrical signals are conducted to IMD 106 from the electrodes via the respective leads 112, 114 and 116 or, in the case of housing electrode 124, a conductor coupled to housing electrode 124. IMD 106 may sense such electrical signals via any bipolar combination of electrodes 126 and 127. Furthermore, any of electrodes 126 and 127 may be used for unipolar sensing in combination with housing electrode 124.

IMD 106 may deliver pacing pulses via a unipolar or bipolar combination of electrodes. IMD 106 delivers pacing pulses via bipolar combinations of electrodes 126 to produce depolarization of cardiac tissue of heart 102. IMD 106 may deliver pacing pulses via any of electrodes 126 in combination with housing electrode 124 in a unipolar configuration. IMD 106 may deliver cardioversion and/or defibrillation shocks to heart 102 via any combination of elongated electrodes 127, and housing electrode 124.

The electrode configuration of system 100 illustrated in FIG. 1 is merely one example electrode configuration. In other examples, a system may include epicardial leads and/or patch electrodes instead of or in addition to the transvenous leads 112, 114 and 116 illustrated in FIG. 1.

Although IMD 106 of FIG. 1 is coupled to three leads 112, 114 and 116, other lead configurations are contemplated. In other words, the number of leads coupled to IMD 106 and the locations of the leads relative to heart 102 may vary. For example, in some alternative implementations, system 100 may include an additional lead or lead segment (not shown in FIG. 1) that deploys one or more electrodes within the left atrium, vena cava, or other vein. The additional lead may allow for alternative electrical sensing configurations that may provide improved sensing accuracy in some patients.

System 100 includes a programmer 130-1 that communicates with IMD 106. Programmer 130-1 may be a handheld computing device, desktop computing device, a networked computing device, or any other type of computing device. Accordingly, programmer 130-1 may be a computing device that includes a computer-readable storage medium having instructions that cause a processor of programmer 130-1 to provide the functions attributed to programmer 130-1 in the present disclosure. System 100 may also include a patient monitor 130-2. Patient monitor 130-2 may be a device that reads data from IMD 106 and uploads the data to a server, e.g., automatically or in response to a command from a patient or other user.

Although shown together in FIG. 1 for ease of illustration, programmer 130-1 and patient monitor 130-2 may, but typically will not, be co-located. Instead, programmer 130-1 and patient monitor 130-2 may individually communicate with IMD 106 when co-located with IMD 106 at respective times. For example, programmer 130-1 may be used by a clinician in a clinical setting to communicate with IMD 106, and patient monitor 130-2 may communicate with IMD 106 in a patient's home, automatically or in response to a user command.

Programmer 130-1 may retrieve data stored in IMD 106 and/or program the operation of IMD 106, e.g., to monitor patient 104 and/or to provide various therapies to patient 104. Programmer 130-1 may also receive data from IMD 106, both in real-time, and data that was stored by the IMD since the last interrogation of the IMD by programmer 130-1. Accordingly, a user may retrieve data from IMD 106 and program IMD 106 using programmer 130-1. For example, the user may include a physician, a technician, a surgeon, an electrophysiologist, or other clinician.

Data retrieved from IMD 106 using programmer 130-1 includes CRT data and sensed cardiac data. The CRT data may include metrics of CRT performance, such as an amount of time that CRT was or was not delivered, which in either case indicates an amount of time that CRT was not delivered. The IMD data may also include other data regarding the delivery of therapy by IMD 106, such as current or past values for parameters that control the delivery of therapy by the IMD.

The sensed cardiac data may include waveforms that indicate electrical activity of heart 102. The waveforms retrieved from the IMD 106 may be referred to as cardiac electrogram waveforms or, more particularly in cases in which the waveforms are detected via an intracardiac electrode, intracardiac electrogram waveforms. Cardiac electrogram waveforms stored by IMD 106 and retrieved by programmer 130-1 may be referred to as "EGMs." Sensed cardiac data retrieved from IMD 106 using programmer 130-1 may also include marker channel data. Marker channel data may indicate the occurrence and timing of sensing, diagnosis, and therapy events associated with IMD 106.

IMD 106 may detect ventricular sense episodes (VSEs). VSEs may be episodes that the IMD detected based on the occurrence of a threshold number of consecutive beats, e.g., 10 beats, that were not paced. VSEs may occur due to ventricular tachyarrhythmia, supraventricular tachyarrhythmia, conducted atrial tachyarrhythmia, an intrinsic rate above the programmed upper tracking rate, or any reason that may cause or allow ventricular depolarizations to occur before expiration of a programmed escape interval, e.g., programmed atrioventricular delay, for CRT pacing. IMD 106 may store EGM and marker channel data for detected VSEs for later retrieval and analysis by a clinician via programmer 130-1. The EGM and marker channel data may include data from the time leading up to and during the VSE detected by IMD 106.

Sensed cardiac data may also include other metrics collected by IMD 106 based on the IMD's analysis of the cardiac electrogram and/or other sensor data. For example, IMD 106 may detect atrial tachyarrhythmia (AT/AF), e.g., atrial tachycardia (AT) or atrial fibrillation (AF). IMD 106 may accumulate time in a counter when the patient is experiencing atrial tachyarrhythmia, which may facilitate a determination of the percent of the period since the last download of data from IMD 106 that patient 104 has experienced atrial tachyarrhythmia. IMD 106 may also accumulate the amount of time that CRT is delivered during AT/AF in another counter, for determination of the percentage of time during AT/AF that CRT is delivered. IMD 106 may also detect the occurrence of premature ventricular contractions (PVCs), and the sensed cardiac data may also include data indicating an amount, e.g., a number, of PVCs, e.g., since the last download of data from the IMD.

The programmer 130-1 may retrieve various types of stored or real-time data from IMD 16, including other sensed physiological parameters of the patient 104, such as intracardiac or intravascular pressure, activity, posture, respiration, or thoracic impedance. Additionally, the stored and retrieved data may include information regarding the performance or integrity of IMD 106 or other components of system 100, such as leads 112, 114 and 116, or a power source of IMD 106. Data regarding performance of IMD 106 may include data indicating the amount of extent of delivery of certain therapies, such as CRT.

A user may program IMD 106 using programmer 130-1. Programming IMD 106 may include, for example, setting values for operational parameters, programming a therapy progression, selecting electrodes used to deliver defibrillation pulses, selecting waveforms for the defibrillation pulses, or selecting or configuring a fibrillation detection algorithm for the IMD 106. In general, a defibrillation pulse may refer to an electrical pulse (i.e., shock) that is delivered to heart 12 to correct a potentially life threatening cardiac arrhythmia such as ventricular fibrillation (VF) or ventricular tachycardia (VT). The user may also use programmer 130-1 to program other therapies provided by IMD 106, such as CRT. For example, the user may use programmer 130-1 to select pacing vectors for CRT, as well as values for a variety of parameters that control the delivery of CRT, such as atrioventricular (A-V) delays, right ventricular to left ventricular (RV-LV) offsets, or other CRT or pacing parameters described herein.

IMD 106 and programmer 130-1 may communicate via wireless communication using any techniques known in the art. Examples of communication techniques may include, for example, low frequency or radiofrequency (RF) telemetry, but other techniques are also contemplated. In some examples, programmer 130-1 may include a programming head that may be placed proximate to the patient's body near an implant site of IMD 106 in order to improve the quality or security of communication between IMD 106 and programmer 130-1.

Patient monitor 130-2 may be a handheld computing device, desktop computing device, a networked computing device, or any other computing device. Patient monitor 130-2 may be a device that the patient uses to transfer data from IMD 106 to a clinic or other remote computing system. For example, patient monitor 130-2 may be a device that patient 104 keeps in their home in order to transfer data from IMD 106 to a clinic or other remote computing system from home. Patient monitor 130-2 may represent a commercially available product, such as a Medtronic CareLink® Monitor developed by Medtronic, Inc., of Minneapolis, Minn.

Patient monitor 130-2 may include similar functionality as programmer 130-1. Specifically, patient monitor 130-2 may retrieve any of various types of stored or real-time data described herein from IMD 106. For example, patient monitor 130-2 may retrieve CRT data and sensed cardiac data, e.g., EGMs and associated marker channels, from IMD 106. Patient monitor 130-2 may transfer data from IMD 106 to a clinic or to a remote device through a network.

Although a high percentage of CRT delivery is desirable, circumstances may arise which inhibit delivery of CRT by an IMD to a patient. For example, atrial, supraventricular, or ventricular tachyarrhythmia, as well PVCs or other arrhythmias, may increase ventricular contraction rates such that ventricular contraction occurs before expiration of the programmed escape interval, which, in this case is the programmed A-V interval. As the amount of loss of CRT therapy delivery is generally of importance to the efficacy of CRT delivered to a patient, it may be beneficial to provide visibility of CRT performance data to clinicians treating patients with CRT. As described herein, the utility of reporting data related to CRT delivery may be improved by presenting CRT performance data correlated to one or more possible reasons for the loss of CRT delivery, such as atrial tachyarrhythmias, PVCs, or VSEs.

IMD 106 may be configured to track and store CRT performance data, including an amount, e.g., percentage, of time CRT delivery occurs and/or the corresponding amount of loss of CRT delivery. Additionally, an IMD may monitor and store data that may form the basis for determining one or more reasons for the loss of CRT delivery, e.g. the occurrence and duration of atrial tachyarrhythmias, the occurrence of PVCs, and the occurrence and duration of VSEs. Based on such data collected by IMD 106, the IMD, programmer 130-1, patient monitor 130-2, and/or another external computing device, such as a remote server device (e.g., remote device 302 of FIGS. 3-5), may apportion the amount of CRT loss determined by the IMD amongst reasons for the loss of CRT, which may be selected from a list of predetermined possible reasons for CRT. One or more such devices may also present the apportionment, e.g., in the form of a report, to enable a user, e.g., clinician, to discern the amount loss of CRT delivery for the patients, and the extent to which different reasons contributed to the loss of CRT delivery.

Figure 2:
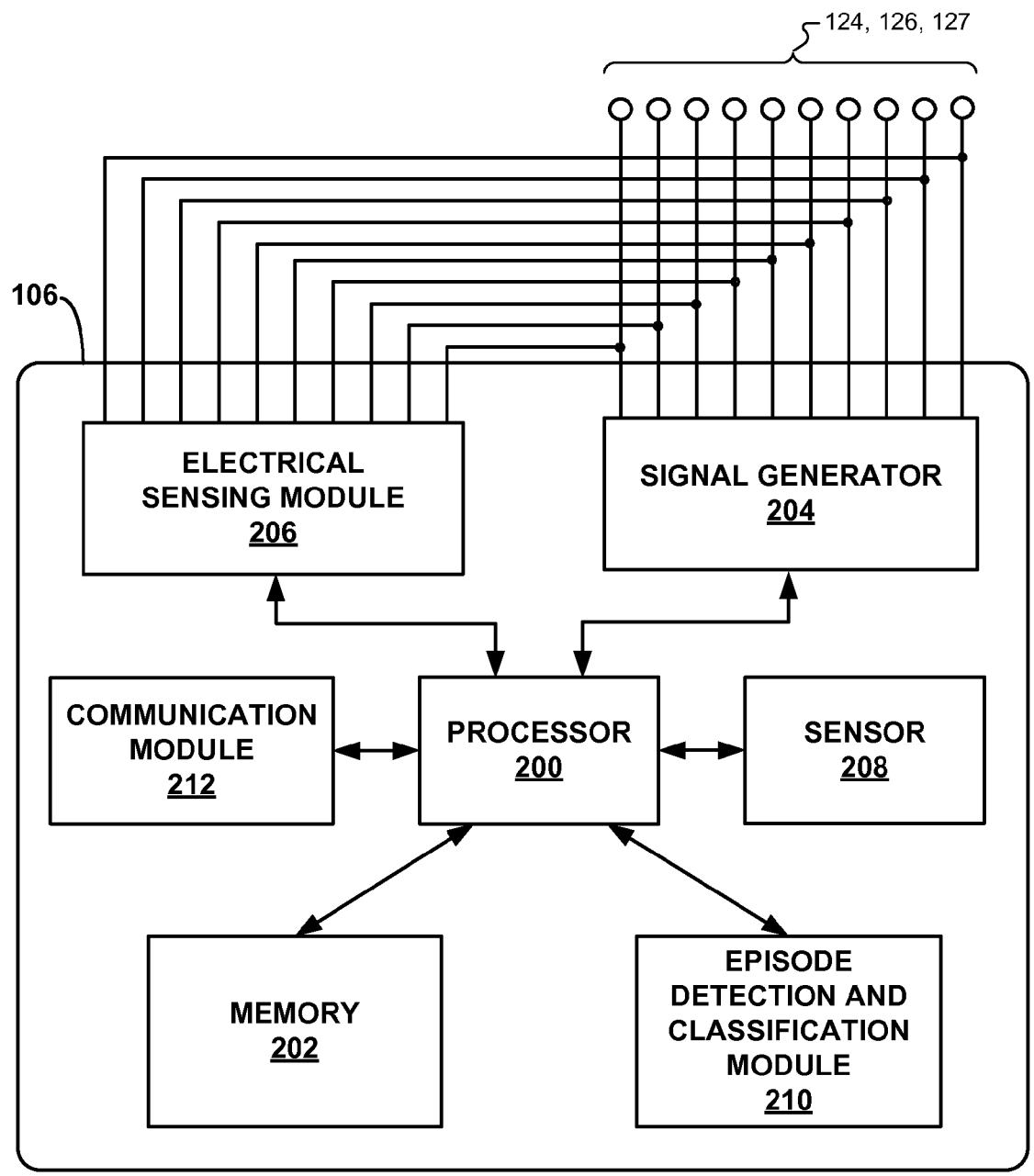
FIG. 2 is a functional block diagram illustrating an example configuration of the IMD of FIG. 1.

FIG. 2 is a functional block diagram illustrating an example configuration of IMD 106. IMD 106 includes a processor 200, memory 202, a signal generator 204, an electrical sensing module 206, a sensor 208, and episode detection and classification module 210, and a communication module 212. Memory 202 may include computer-readable instructions that, when executed by processor 200, cause IMD 106 and processor 200 to perform various functions attributed to IMD 106 and processor 200 herein. Memory 202 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other digital media.

Processor 200 may include any one or more of a microprocessor, a microcontroller, a digital signal processor (DSP), an application specific integrated circuit (ASIC), a field-programmable gate array (FPGA), or equivalent discrete or integrated logic circuitry. In some examples, processor 200 may include multiple components, such as any combination of one or more microprocessors, one or more microcontrollers, one or more DSPs, one or more ASICs, or one or more FPGAs, as well as other discrete or integrated logic circuitry. The functions attributed to processor 200 herein may be embodied as software, firmware, hardware or any combination thereof.

Signal generator 204 is electrically coupled to electrodes 124, 126 and 128, e.g., via conductors of the respective leads 112, 114 and 116, or, in the case of housing electrode 124, via an electrical conductor disposed within housing 108 of IMD 106. Signal generator 204 is configured to generate and deliver electrical stimulation therapy to heart 102. For example, signal generator 204 may deliver defibrillation pulses to heart 102 via at least two of electrodes 124 and 127. Signal generator 204 may deliver pacing pulses, e.g., for CRT, via any two or more of electrodes 124 and 126. In some implementations, signal generator 204 delivers pacing, cardioversion, or defibrillation stimulation in the form of electrical pulses. In other implementations, signal generator 204 may deliver one or more of these types of stimulation in the form of other signals, such as sine waves, square waves, or other substantially continuous time signals.

Processor 200 may control the delivery of stimulation therapy by signal generator 204. More particularly, processor 200 may control signal generator 204 to deliver stimulation, such as CRT, according to selected values for a plurality of operational parameters, which may be stored in memory 202. Amongst other parameters, processor 200 may select via which vector stimulation is delivered, i.e., via which electrodes the stimulation is delivered.

Electrical sensing module 206 monitors signals from at least one of electrodes 124, 126 and 127 in order to monitor electrical activity of heart 102. Processor 200 may select via which sensing vector or vectors the electrical activity is monitored, i.e., which of electrodes 124, 126 and 127 function as sense electrodes. The sensing vector selection by processor 200 may be based on programmable operational parameters stored in memory 202. In some examples, electrical sensing module 206 may include multiple channels, each coupled to a respective sensing vector, and each configured to provide an indication, e.g., to processor 200 and/or episode classification and detection module 210, upon sensing a particular event, such as an R-wave, P-wave, in a particular chamber of heart 102.

Processor 200 may implement programmable counters. For delivery of pacing pulses to heart 102, such counters may control the basic time intervals associated with DDD, VVI, DVI, VDD, AAI, DDI, DDDR, VVIR, DVIR, VDDR, AAIR, DDIR and other modes of pacing. Such counters may control various time intervals associated with delivery of CRT, such as A-V intervals, V-A intervals, V-V intervals, A-A intervals, or RV-LV offsets. The durations of these intervals may be programmable, e.g., via programmer 130-1 or patient monitor 130-2, and determined by processor 200 in response to stored data in memory 202.

In some examples, memory 202 may store two A-V intervals, an SAV interval and PAV interval, as programmable parameters that control pacing and, more particularly, CRT. The SAV interval may be an escape interval used by processor 200 to time delivery of one or more ventricular pulses from a sensed atrial event, e.g., depolarization, while the PAV is used to time delivery of one or more ventricular pulses from a paced atrial event. The RV-LV offset may be an interval, e.g., escape interval, which defines the relationship between paced or intrinsic depolarizations in the left and right ventricles. For example, the RV-LV offset may define the interval between delivery of pacing pulses to the ventricles in bi-ventricular pacing for CRT. The intervals may also include refractory periods during which sensed P-waves and R-waves are ineffective to restart timing of such escape intervals, and blanking intervals to withhold sensing from one or more channels of sensing module 206 for a time interval during and after delivery of electrical stimulation to heart 102.

A portion of memory 202 may be configured as a plurality of recirculating buffers, capable of holding a series of measured intervals, which may be analyzed by episode detection and classification module 210 to determine whether the patient's heart 102 is presently exhibiting atrial or ventricular tachyarrhythmia. Episode detection and classification module 210 may detect tachyarrhythmia using any suitable tachyarrhythmia detection algorithm. In the event that episode detection and classification module 210 detects an atrial or ventricular tachyarrhythmia, a responsive therapy, e.g., anti-tachycardia pacing (ATP), cardioversion, or defibrillation, may be loaded by processor 200 and implemented using signal generator 204.

Episode detection and classification module 210 may also detect VSEs. For example, episode detection and classification module 210 may detect a VSE based on the occurrence of greater than a threshold number, e.g., 10, of consecutive sensed ventricular events. Episode classification and detection module 210 may be implemented as a hardware module separate from processor 200, a software module executed by processor 200, or a combination of hardware and software modules, in some examples.

IMD 106 may include one or more sensors, such as sensor 208. Sensor 208 may comprise a pressure sensor (e.g., a capacitive sensor) that senses intracardiac or other cardiovascular pressure. Sensor 208 may comprise a motion sensor. The motion sensor may be, for example, an accelerometer or piezoelectric element. Sensor 208 may also comprise a heart sound sensor, or any sensor capable of generating a signal that varies as a function of mechanical activity, e.g., contraction of heart 102. Processor 200 may receive one or more signals from sensor 208 or a plurality of sensors. Processor 200 may monitor, among other things, the mechanical activity of heart 102 based on signals from the one or more sensors.

Sensor 208 may be positioned in various locations in diagnostic system 100. For example, sensor 208 may be located within housing 108, outside of housing 108, or on or within on or more of leads 112, 114, or 116. Sensor 208 may communicate with IMD 106 via wireless communication when sensor 208 is located outside of housing 108. In some implementations, sensor 208 may be external (i.e., not implanted).

Communication module 212 includes any suitable hardware, firmware, software or any combination thereof for communicating with another device, such as programmer 130-1 and/or patient monitor 130-2. Under the control of processor 200, communication module 212 may receive downlink telemetry from and send uplink telemetry to programmer 130-1 and/or patient monitor 130-2 with the aid of an antenna (not shown), which may be internal and/or external. Processor 200 may provide the data to be uplinked to programmer 130-1 and/or patient monitor 130-2 and the control signals for telemetry circuitry within communication module 212, e.g., via an address/data bus.

For example, processor 200 may provide stored and/or real-time EGMs to programmer 130-1 and/or patient monitor 130-2 via communication module 212. The stored EGMs may be associated with VSEs detected by episode classification and detection module 210, e.g., stored in response to detection or diagnosis of a VSE by episode classification and detection module 210. Processor 200 may store the EGMs in memory 202, and retrieve the stored EGMs from memory 202.

Processor 200 may also generate marker channel data, and store marker channel data, e.g., associated with detected VSEs, in memory 202. Marker channel data may indicate the occurrence and timing of sensing, diagnosis, and therapy events, e.g., P-waves, R-waves, tachyarrhythmia (e.g., tachycardia or fibrillation), pacing pulses, anti-tachycardia pacing (ATP), cardioversion shocks, or defibrillation shocks, detected, diagnosed, or undertaken by IMD 106. Programmer 130-1 and/or patient monitor 130-2 may interrogate IMD 106, via communication module 212, to receive the marker channel data. Processor 200 may also provide the marker channel data to programmer 130-1 and/or patient monitor 130-2 in real-time via communication module 212, e.g., when the marker channel data is generated.

Processor 200 may store EGMs and marker channel data corresponding to VSEs or tachyarrhythmias in memory 202. Processor 200 may also store EGMs and marker channel data corresponding to nonsustained tachycardia (NST) in memory 202 in response to detection of the NST using any suitable NST detection technique. An NST is an episode in which a threshold number of V-V intervals met a rate criterion for tachyarrhythmia detection, but the number of intervals was fewer than a higher number of intervals to detect (NID) ventricular tachyarrhythmia. VSEs may include NSTs, in some examples. Programmer 130-1 and/or patient monitor 130-2 may interrogate IMD 106, via communication module 212, to receive the stored EGMs and marker channels.

Processor 200 may also store other data in memory 202, such as other data relating to cardiac sensing by IMD 106, the programming of IMD 106, and the performance, e.g., delivery of therapy, by IMD. The data may include, for example, the programmed settings/algorithms of IMD 106, e.g., at the time an episode was detected/treated. Programming or parameter data stored by IMD 106 and provided to one both of programmer 130-1 and patient monitor 130-2 may include pacing modes for pacing, e.g., CRT, sensed and programmed A-V or other interval times, e.g., RV-LV offsets, upper and lower tracking rates (or associated interval lengths), and a number of other CRT programming features, including conducted AF response, atrial tracking recovery, and ventricular sense response.

The data stored by IMD 106 and available to programmer 130-1 and patient monitor 130-2 may also include amounts of time that CRT was or was not delivered, e.g., overall or during certain other conditions of the patient or IMD, such as during atrial tachyarrhythmia. The data may also include data indicating incidences of atrial tachyarrhythmia, e.g., AT or AF, and the overall amount of time patient 104 experienced atrial tachyarrhythmia, as well as the number of PVCs. Programmer 130-1 and/or patient monitor 130-2 may interrogate IMD 106, via communication module 212, to receive such data.

Figure 3:
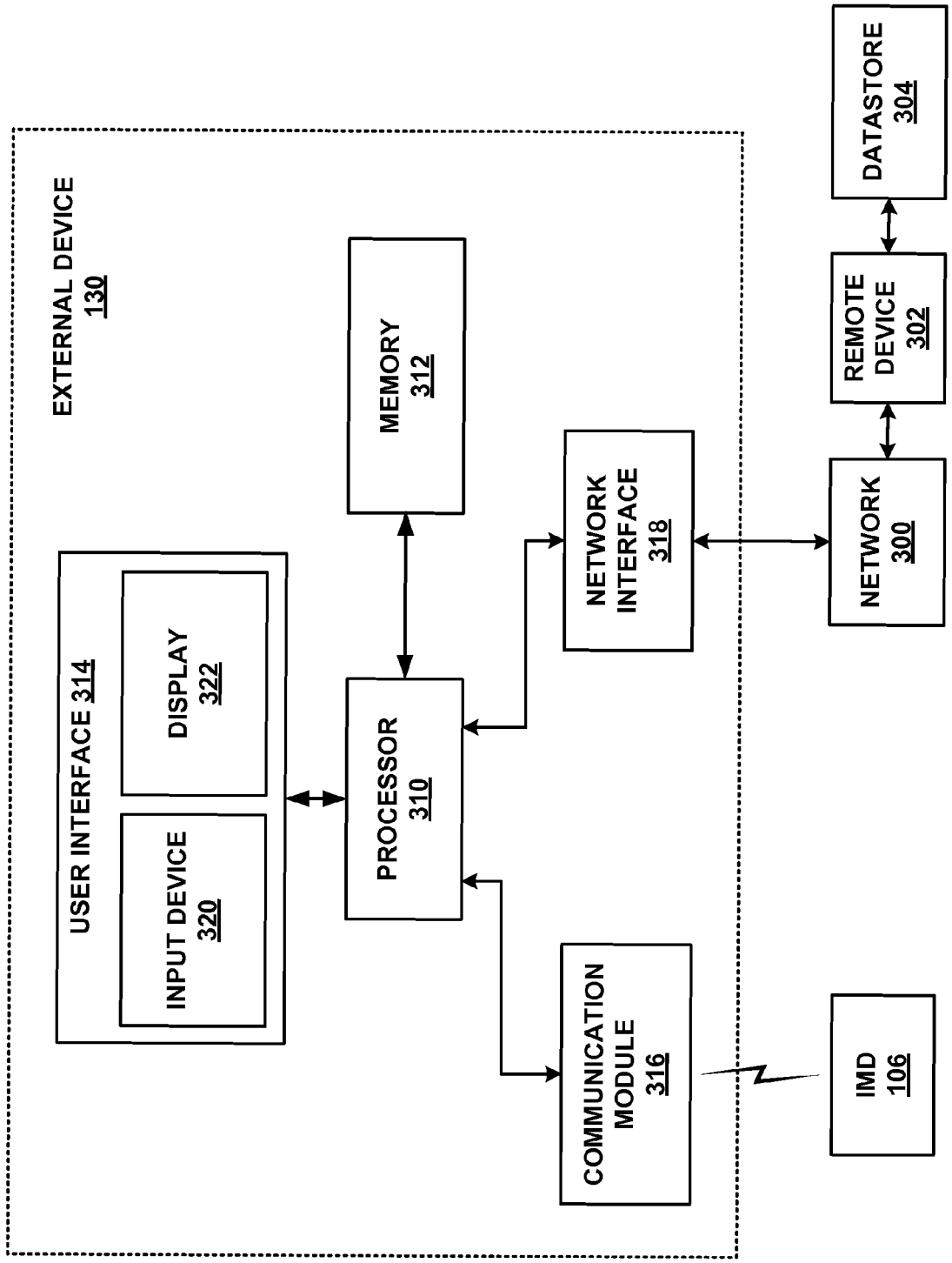
FIG. 3 is a functional block diagram illustrating the IMD of FIG. 1 in communication with a remote device via an external device and a network.

FIG. 3 is a functional block diagram illustrating an example configuration of an external device 130, such as programmer 130-1 or patient monitor 130-2. In other examples, external device 130 may take the form of any external computing device configured to communicate with IMD 106, such as a cellular telephone. External device 130 communicates, e.g., wirelessly, with IMD 106, as described above. External device 130 may also communicate with other computing devices, e.g., to provide data retrieved from IMD 106 to such computing devices. In the illustrated example, external device 130 communicates with a remote device 302, e.g., a remote server device, via a network 300. As illustrated in FIG. 3, remote device 302 may communicate with a data store 304, which may store data that has been retrieved from IMD 106 by external device 130 and transmitted to remote device 302 via network 300. External device 130 may retrieve any of data described herein that is stored by IMD 106 from the IMD periodically, e.g., nightly, weekly, or monthly, or during clinic appointments.

External device 130 includes a processor 310, memory 312, a user interface 314, a communication module 316, and a network interface 318. External device 130 may be a dedicated hardware device with dedicated software for communicating with IMD 106. For example, external device 130 may be a dedicated hardware device that programs operational parameters of IMD 106 and/or receives data from IMD 106. Alternatively, external device 130 may be an off-the-shelf computing device, such as a desktop or laptop computer, running an application that enables external device 130 to communicate with IMD 106 (i.e., receive data from IMD 106 and/or program IMD 106). Accordingly, external device 130 represents any computing device capable of performing the functions attributed to external devices 130 in the present disclosure.

The user interacts with external device 130 using user interface 314. User interface 314 includes an input device 320 and a display 322 (e.g., an LCD display). The user enters data into external device 130 using input device 320. Input device 320 may include various devices for entering data. Input device 320 may include a keypad, for example, an alphanumeric keypad or a reduced set of keys associated with particular functions of external device 130. Input device 320 may also include a freehand peripheral input device such as a mouse, a stylus, and a touchscreen. In some examples, such as those in which external device 130 is a patient monitor 130-2, external device 130 need not include some or all of the functionality of user interface 314, e.g., may not include input device 320 and/or display 322.

External device 130 may communicate wirelessly with IMD 106, such as using RF communication or proximal inductive interaction. This wireless communication is possible through the use of communication module 316, which may be coupled to an internal antenna or an external antenna. Communication module 316 may include similar functionality as communication module 212 of IMD 106.

Network interface 318 of external device 130 may communicate with remote device 302 via network 300. Remote device 302 may include, for example, a general purpose computing device such as an off-the-shelf desktop/laptop computer or server computer configured to communicate with external device 130 via network 300. Network 300 may include various types of networks, such as a wide area network (WAN) and/or the Internet, for example. Although network 300 may represent a long range network (e.g., Internet or WAN), in some implementations, network 300 may be a shorter range network, such as a local area network (LAN).

Processor 310 can take the form of one or more microprocessors, DSPs, ASICs, FPGAs, programmable logic circuitry, or the like, and the functions attributed to processor 310 herein may be embodied as hardware, firmware, software or any combination thereof. Processor 310 of external device 130 may provide any of the functionality ascribed herein, or otherwise perform any of the methods described herein.

Memory 312 may store instructions that cause processor 310 to provide the functionality ascribed to external device 130 herein. Memory 312 may also store information used by processor 310 to provide the functionality ascribed to external device 130 herein. Memory 312 may include any fixed or removable magnetic, optical, or electrical media, such as random access memory (RAM), read-only memory (ROM), compact-disc ROM (CD-ROM), hard or floppy magnetic disks, electrically erasable programmable ROM (EEPROM), or the like. Memory 312 may also store information that controls therapy delivery by IMD 106.

External device 130 may store data in a datastore 304. For example, processor 310 may transfer data to remote device 302, which then transfers the data to datastore 304. Accordingly, remote device 302 may be a server that communicates with external device 130 to store data from external device 130 in datastore 304 and retrieve data from datastore 304 for use by external device 130. Datastore 304 may include any type of computer data storage or computer memory for storing data received from remote device 302. For example, datastore 304 may include magnetic storage media (e.g., hard disk drives), optical media (e.g., digital versatile disc drives), and/or solid state memory (e.g., dynamic random access memory or EEPROM). Additionally, datastore 304 may include a software based data storage and retrieval mechanism, including an off-the-shelf or proprietary database.

In some implementations, remote device 302 and datastore 304 may include network technology and functionality similar to that provided by the Medtronic CareLink® Network developed by Medtronic, Inc., of Minneapolis, Minn. The data stored in datastore 304 may include, for example, EGMs, marker channel data, other sensed cardiac data, or any other data received from IMD 106. In other implementations, remote device 302 and datastore 304 may represent or interface with a system configured to store electronic medical records, which may additionally or alternatively include other waveforms or medical information for patient 104.

Figure 4:
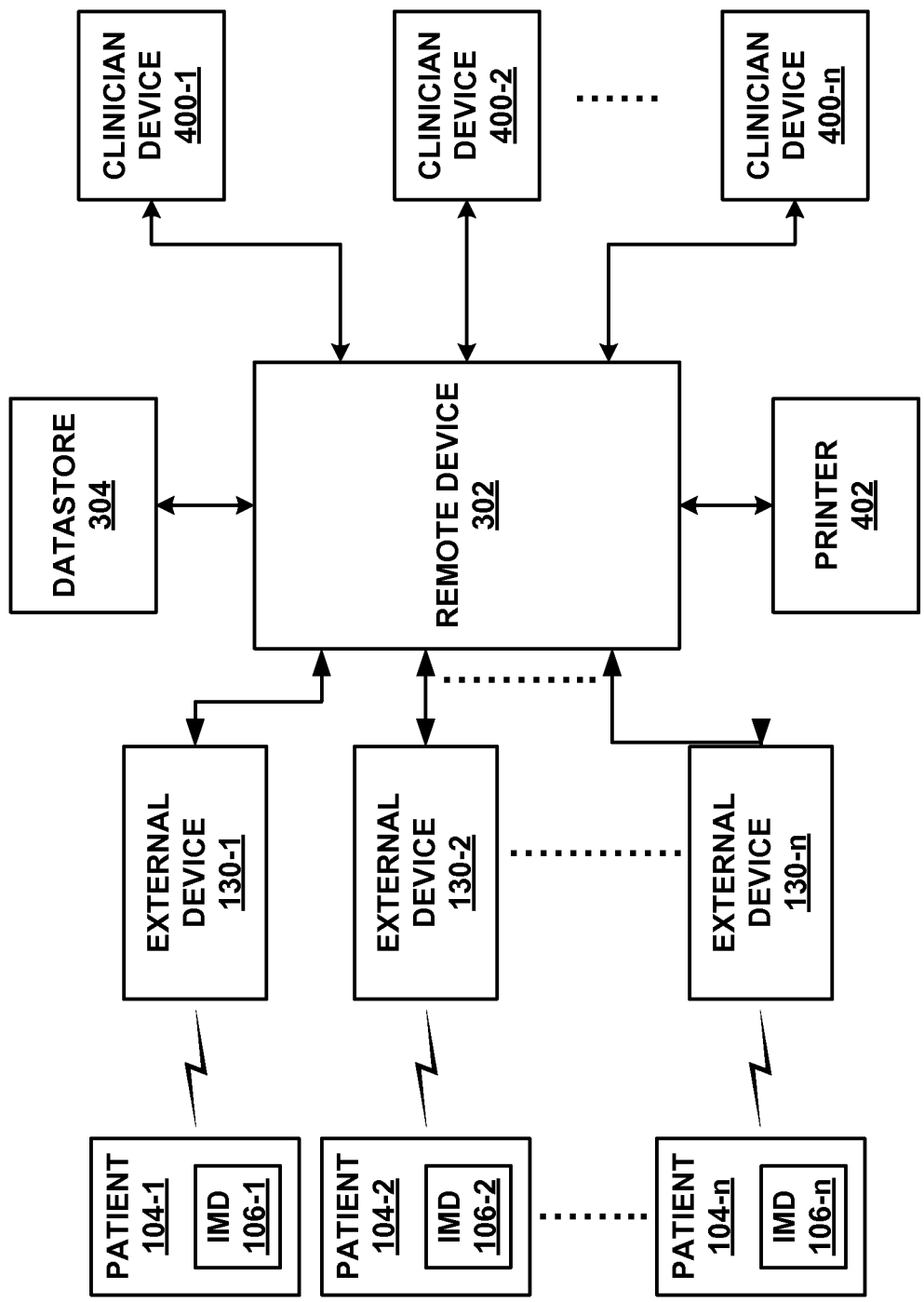
FIG. 4 is a functional block diagram illustrating the remote device of FIG. 3 in communication with a plurality of devices, including with a plurality of IMDs via a plurality of external devices.

FIG. 4 is a functional block diagram illustrating remote device 302 in communication with a plurality of devices, including with a plurality of IMDs 106-1, 106-2, . . . , and 106-*n* (collectively "IMDs 106") implanted in different patients 104-1, 104-2, . . . , and 104-*n* (collectively "patients 104") via a plurality of external devices 130-1, 130-2, . . . , and 130-*n* (collectively "external devices 130").

Remote device 302 may be a computing device (e.g., a server) that is connected to external devices 130 through network 300 (FIG. 3). Since patients 104 may be located in various clinics or residences apart from one another, e.g., across the United States or across the globe, external devices 130 may connect to remote device 302 through various long range networks, such as a WAN and/or the Internet. Although remote device 302 is described as being connected to external devices 130 through a long range network, in some implementations, remote device 302 may be connected to external devices 130 through a shorter range network, such as a LAN.

Remote device 302 may store data received from external devices 130, which may have in turn been received from IMDs 106, in datastore 304, and may also retrieve stored data from datastore 304. Data stored in and retrieved from datastore 304 may include, for example, EGMs, marker channel data, or other data retrieved from IMDs 106, as described herein.

Datastore 304 may be accessed by one or more clinician devices 400-1, 400-2, . . . , and 400-n (collectively "clinician devices 400"). Clinician devices 400 may represent any general computing device used (e.g., by clinicians) to communicate with remote device 302, such as general purpose desktop/laptop computers. Clinician devices 400 or programmers 130-1 may be used by clinicians to access data collected from IMDs 106 and stored in datastore 304. Clinician devices 400 may provide a convenient mechanism to monitor a patient and/or IMD between clinic visits.

Each of clinician devices 400 of FIG. 4 may be associated with a different clinician or clinic. Clinics may be operated by one or more clinicians that have implanted IMDs 106 or that provide follow-up services associated with the IMDs 106. Accordingly, each of clinician devices 400 may represent a general computing device that may be used by a clinician to access datastore 304 to retrieve data regarding IMDs 106 with which the clinician is associated.

Generally, clinician devices 400 may represent computing devices that are remotely located from one another. For example, each clinician device 400 may represent a different computing device located at a different clinic, for example, across the United States, or across the globe. Since the clinics may be located remotely from one another, clinician devices 400 may connect to remote device 302 through various long range networks such as the Internet, a WAN, etc. Although clinician devices 400 are described as being connected to remote device 302 through a long range network, in some implementations, clinician devices 400 may be connected to remote device 302 through a shorter range network, such as a LAN.

In general, presentation of any data or other representation to a user described herein may be implemented via a clinician device 400 or an external device 130. As illustrated in FIG. 4, remote device 302 may also be coupled, e.g., via a network, to a printer 402. Printer 402 may additionally or alternatively be coupled to one of external devices 130 or clinician devices 400. In some examples, presentation of any data or other representation to a user described herein may be via a document printed by printer 402.

Figure 5:
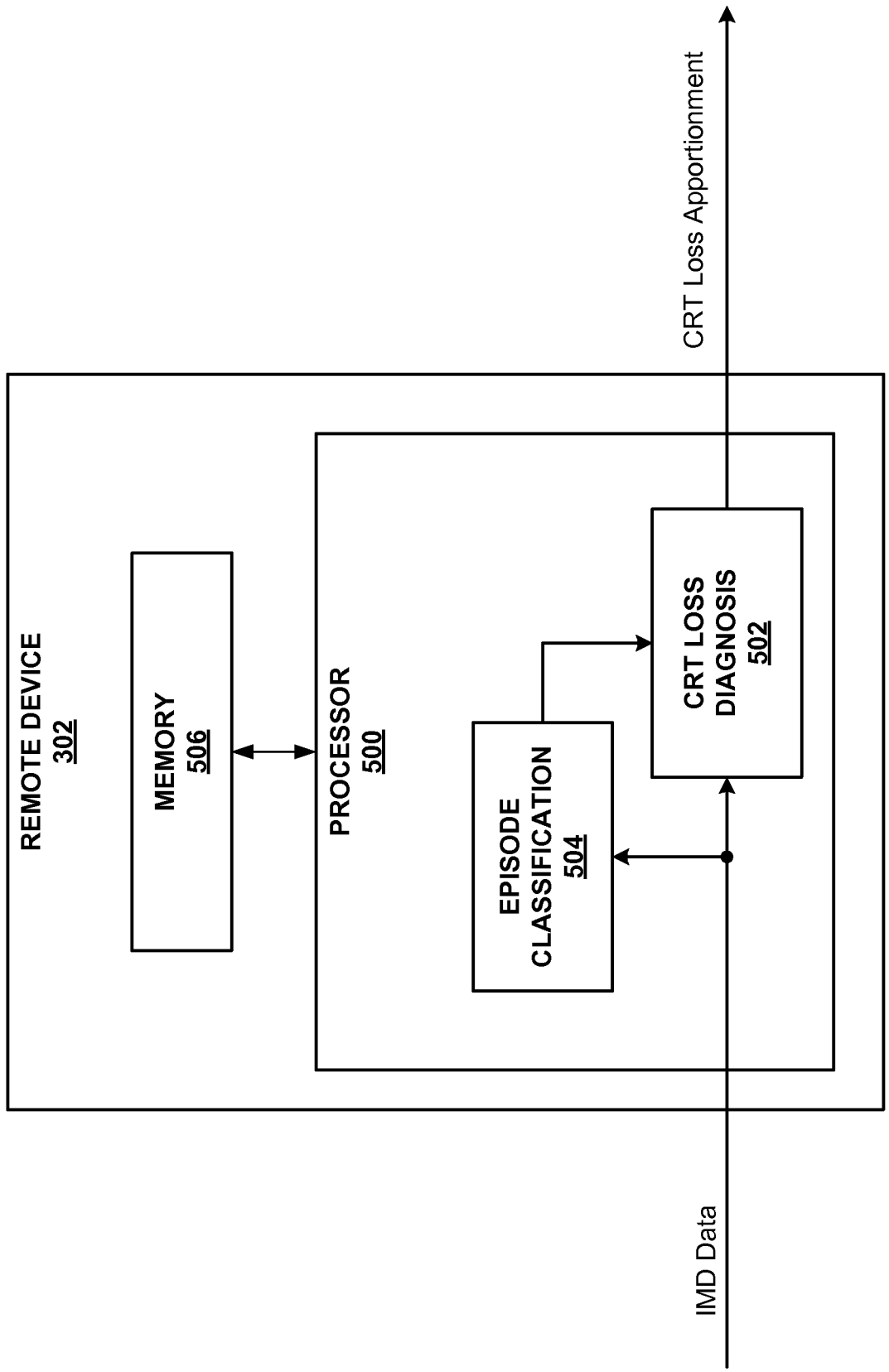
FIG. 5 is a functional block diagram illustrating an example configuration and operation of the remote device of FIG. 3.

FIG. 5 is a block diagram illustrating an example configuration and operation of remote device 302. Remote device 302 may include, for example, a general purpose computing device. Remote device 302, and modules included in remote device 302, may be implemented, at least in part, in hardware, software, firmware or any combination thereof.

In the illustrated example, remote device 302 includes a processor 500 and a memory 506. Processor 500 may comprise one or more processors within one or more physical devices, including one or more microprocessors, DSPs, ASICs, FPGAs, or any other equivalent integrated or discrete logic circuitry, as well as any combinations of such components. When implemented in software, the functionality ascribed to remote device 302 may be embodied as instructions on a computer-readable medium, such as memory 506, which may include any one or more of RAM, ROM, NVRAM, EEPROM, FLASH memory, magnetic data storage media, optical data storage media, or the like. The instructions may be executed by processor 500 to support one or more aspects of the functionality of remote device 302 described in this disclosure.

In the example of FIG. 5, processor 500 includes a CRT loss diagnosis module 502 and an episode classification module 504. CRT loss diagnosis module 502 and episode classification module 504 may be implemented as hardware modules separate from processor 500. In the illustrated example, CRT loss diagnosis module 502 and episode classification module 504 are implemented by processor 500, e.g., as software modules executed by the processor. In one example, instructions or other data or information used by processor 500 to execute and carry out the functions of diagnosis module 502 and episode classification module 504 may be stored in memory 506.

As illustrated in FIG. 5, processor 500 receives IMD data, which may include CRT data, sensed cardiac data, and any other data described herein. Processor 500 may receive the IMD data from IMD 106, e.g., during a download of data from the IMD. Processor 500 may receive, e.g., retrieve, IMD data previously stored for IMD 106 in data store 304.

CRT loss diagnosis module 502 and episode classification module 504 may analyze respective, but not necessarily exclusive, subsets of the IMD data, as described in greater detail below with respect to FIGS. 6-12. In general, CRT loss diagnosis module 502 receives CRT data from IMD 106 that indicates an amount of time that CRT was not delivered to the patient. The CRT data may be percentage of a period, e.g., since last the last download from IMD 106, that CRT was, or was not, delivered. Where IMD 106 collects and provides the percentage of CRT, CRT loss diagnosis module 502 may determine an amount, e.g., percentage, of loss of CRT, by subtracting the amount of CRT from the total, e.g., 100%.

CRT loss diagnosis module 502 also receives at least some of the sensed cardiac data from IMD 106. Such data may indicate the occurrence and amounts of atrial tachyarrhythmias, PVCs, and VSEs, as examples. CRT loss diagnosis module 502 apportions the amount of time that CRT was not delivered amongst predetermined reasons for CRT loss, such as atrial tachyarrhythmias, PVCs, and VSEs, based on the sensed cardiac data.

In some examples, CRT loss diagnosis module 502 apportions the VSE-based CRT loss amongst a plurality of predetermined VSE classifications. Episode classification module 504 analyzes sensed cardiac data from IMD 106 that IMD 106 stored for VSEs detected by the IMD. The sensed cardiac data for VSEs stored by IMD 106 and analyzed by episode classification module 504 may include EGMs and associated marker channels, as examples, but may include other data as well, as described below. Episode classification module 504 may implement the VSE classification techniques described below with respect to FIGS. 8-12. In some examples, episode classification module 504 may additionally or alternatively implement other techniques, such as those described in U.S. patent application Ser. No. 11/564,120, filed Nov. 28, 2006, titled "Method and Apparatus for Post-Processing of Episodes Detected by a Medical Device," which is incorporated herein by reference in its entirety.

The CRT loss apportionment determined by CRT loss diagnosis module 502 may be presented to a user. The presentation may be in the form of a list of reasons for CRT loss and associated portions, e.g., percentages, of CRT loss attributable to the reasons. The percentages apportioned to each of the reasons may be percentages of the loss, for which a sum of the percentages associated with the predetermined reasons will be equal or approximately equal to 100%. In other examples in which the amount of time of CRT loss is a percentage of a total period of time, e.g., since the last download from the IMD, the percentages apportioned to the predetermined reasons may be percentages of the total period of time. In such examples, the sum of the percentages associated with the predetermined reasons will be approximately equal to the percentage of the period that CRT was not delivered, e.g., the % loss CRT. In some examples, the presentation may be in the form of a pie chart, bar graph, histogram or other graphical illustration of the relative contributions of the various reasons for CRT loss.

Remote device 302 may include a user interface (not shown) for the presentation of the CRT loss apportionment, or other computing devices, e.g., clinician devices 400 or external devices 130 may present the CRT loss apportionment. A presentation of CRT loss apportionment may be output by printer 402, in some examples. A user, such as a clinician may modify one or more programmable parameters that affect the delivery of CRT by IMD 106 based on the CRT loss apportionment. In some examples, processor 500 may analyze the apportionment, and recommend programming changes to the user based on the analysis.

Although described herein as implemented in remote device 302, CRT loss diagnosis module 502 and/or episode classification module 504, as well as the functionality attributed to processor 500, may be implemented in any one or more computing devices, e.g., processors thereof, such as IMD 106, external devices 130, or clinician devices 400. Accordingly, the example methods described below with respect to FIGS. 6-12 may be implemented in any one or more of a remote device 302, IMD 106, external devices 130, or clinician devices 400.

Figure 6:
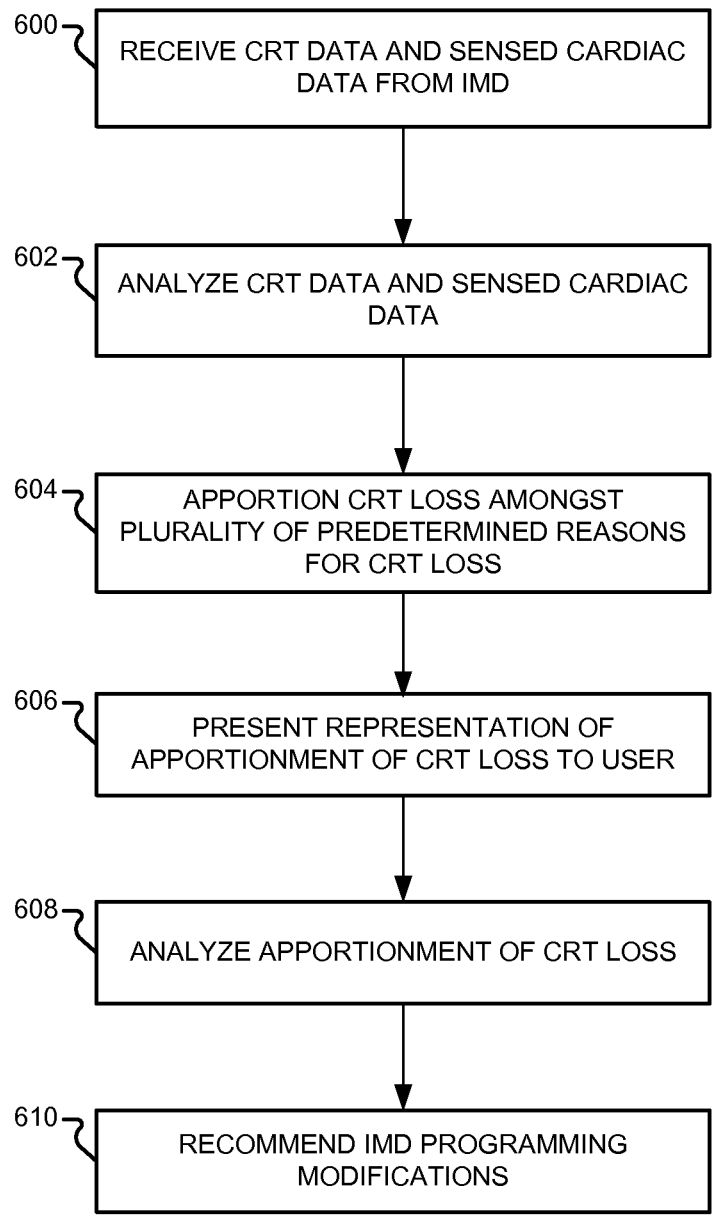
FIG. 6 is a flow diagram illustrating an example method that includes apportioning CRT loss amongst a plurality of reasons for CRT loss.

FIG. 6 is a flow diagram illustrating an example method that includes apportioning CRT loss amongst a plurality of reasons for CRT loss. According to the example method, processor 500 receives CRT data and sensed cardiac data from IMD 106, e.g., during transmission by the IMD or from data store 304 (600). The CRT data may indicate an amount of CRT loss. CRT loss diagnosis module 502 analyzes the CRT data and sensed cardiac data (602), and apportions CRT loss amongst a plurality of predetermined reasons for CRT loss, such as atrial tachyarrhythmia, PVCs and VSEs, based on the analysis (604).

A computing device, such as server 302, external devices 130, computing devices 400, or printer 402, presents the apportionment of CRT loss to a user (606). The presentation of the apportionment may be via a list of reasons for CRT loss with associated amounts of loss, or via a pie chart or other graphical illustration divided or configured according to the apportionment. Processor 502 may also analyze the apportionment of CRT loss (608), and automatically recommend modifications to the programming of IMD 106, e.g., to programmable parameters that affect the delivery of CRT by the IMD, to a user (610). As one example, if AF is a significant reason for loss of CRT, e.g., due to conduction of the fast rate to the ventricles, a change to a non-tracking pacing mode, such as a VVI or DDI mode, may be suggested by processor 502 to facilitate delivery of CRT during AF. As another example, if VSEs with short intrinsic A-V intervals are a significant reason for loss of CRT, processor 502 may suggest lowering the programmed SAV to facilitate delivery of CRT during the VSEs.

Some data from some IMDs or patients may be excluded from analysis according to the method of FIG. 6 for a variety of reasons. For example, if CRT is intentionally turned off, or pacing is set to an RV-only or an ODO mode, the analysis of FIG. 6 may not be beneficial. Furthermore, if sensed cardiac data from the IMD does not include data from an atrial or LV lead, or if such data is potentially unreliable, the patient, IMD or data may be excluded from analysis according to the method of FIG. 6. Absent or unreliable atrial or LV data may be indicated by atrial or LV lead impedance or associated sense amplifier sensitivity.

Figure 7:
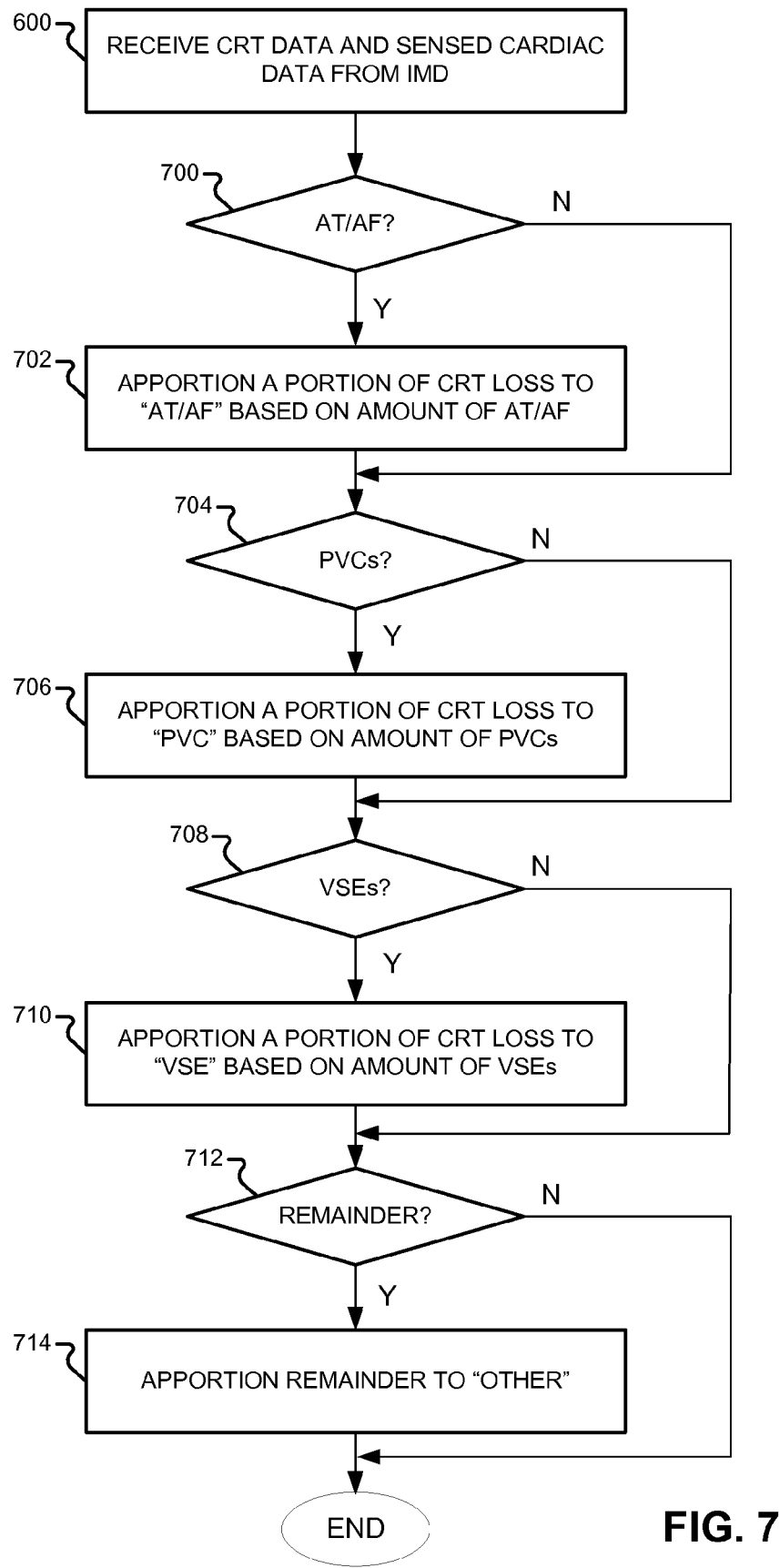
FIG. 7 is a flow diagram illustrating an example method for apportioning CRT loss amongst a plurality of reasons for CRT loss.

FIG. 7 is a flow diagram illustrating an example method for apportioning CRT loss amongst a plurality of reasons for CRT loss. According to the example method, processor 500 receives CRT data and sensed cardiac data from IMD 106 (600). Items 700-714 of the example method of FIG. 7 generally provide more detail regarding one example of analyzing CRT data and sensed cardiac data (602 of FIG. 6), and apportioning CRT loss amongst a plurality of predetermined reasons for CRT loss (604 of FIG. 6).

As described above, sensed cardiac data stored by IMD 106 may include an amount of atrial tachyarrhythmia, e.g., an amount of AT/AF, since the last download from IMD 106. The amount may be stored by IMD 106 by accumulating a counter during AT/AF, and may be represented in seconds, minutes, or some other denomination of time. In some examples, the counter may only be incremented if the AT/AF is accompanied by a fast ventricular rate. The sensed cardiac data may also include an amount, e.g., number, of PVCs detected by IMD 106 since last download, which IMD 106 may track with one or more counters. The sensed cardiac data may also include an amount, e.g., in number or in accumulated time (seconds) of VSEs detected or diagnosed by IMD 106.

According to the example method of FIG. 7, CRT loss diagnosis module 502 determines whether the sensed cardiac data indicates any amount of time of AT/AF (700). If the sensed cardiac data indicates AT/AF ("Y" branch of 700), CRT loss diagnosis module 502 apportions a portion of the CRT loss indicated by the CRT data from IMD 106 to "AT/AF" (as one predetermined reason for CRT loss) based on the amount of AT/AF (702). In one example, the sensed cardiac data may include hours in AT/AF since the last download session, and the CRT data may include a percentage of time that CRT was delivered during AT/AF. CRT loss diagnosis module 502 may determine the percentage of AT/AF hours during the period of time since the last download, and multiply that by 100%—the percentage of CRT during AT/AF. The resulting product of the multiplication may be percentage of CRT loss apportioned to AT/AF. If the sensed cardiac data does not indicate AT/AF ("N" branch of 700), CRT loss diagnosis module 502 may proceed to investigate others of the predetermined reasons for CRT loss.

Either after apportioning CRT loss to AT/AF, or otherwise, CRT loss diagnosis module 502 may determine whether the sensed cardiac data indicates any sensed PVCs (704). If the sensed cardiac data indicates PVCs ("Y" branch of 704), CRT loss diagnosis module 502 apportions a portion of the CRT loss indicated by the CRT data from IMD 106 to "PVC" (as one predetermined reason for CRT loss) based on the amount of PVCs (706). In one example, IMD 106 increments a first counter when a PVC is detected, and increments a second counter when a run of PVCs is detected. Based on estimates of the number of PVCs in a run and the time per PVC, CRT loss diagnosis module 502 may estimate a percentage of time that PVCs are occurring based on the first and second counter data from IMD 106, and thereby estimate the percentage of the total CRT loss attributable to PVCs as the portion of CRT loss apportioned to PVCs. If the sensed cardiac data does not indicate PVCs ("N" branch of 704), CRT loss diagnosis module 502 may proceed to investigate others of the predetermined reasons for CRT loss.

Either after apportioning CRT loss to PVCs, or otherwise, CRT loss diagnosis module 502 may determine whether the sensed cardiac data indicates any detected or diagnosed VSEs (708). If the sensed cardiac data indicates VSEs ("Y" branch of 708), CRT loss diagnosis module 502 apportions a portion of the CRT loss indicated by the CRT data from IMD 106 to "VSE" (as one predetermined reason for CRT loss) based on the amount of VSEs (710). In one example, IMD 106 accumulates time, e.g., increments a duration counter, based on the duration of detected VSEs. Based on this total VSE duration, CRT loss diagnosis module 502 may determine the percentage of the total time since last download during which VSEs occurred, and thereby estimate the percentage of the total CRT loss attributable to VSEs as the portion of CRT loss apportioned to VSEs.

CRT loss diagnosis module 502 may subtract from the VSE duration value provided by IMD 106 the duration of any VSE that occurred during AT/AF, e.g., for which the VSE may have been caused by conducted AT/AF. In this manner, CRT loss diagnosis module 502 may avoid double-counting the impact of such episodes on loss of CRT, e.g., apportioning CRT loss to both AT/AF and VSEs based on such episodes. Furthermore, because the amounts, e.g., percentages, of CRT loss apportioned to the various predetermined reasons by CRT loss diagnosis module 502 may be based on estimates, CRT loss diagnosis module 502 may ensure that the sum of the portions of the CRT loss apportioned to the predetermined reasons do not exceed the total, e.g., do not exceed 100%. For example, if at any of 702, 706 and 710 of the example method of FIG. 7 the sum of the portions exceeds the total CRT loss, CRT loss diagnosis module 502 may reduce the most recently estimated portion so that the sum of the portions equals the total CRT loss amount. The reasons for loss of CRT (AT/AF, PVCs, VSEs) illustrated in FIG. 7 are examples. In other examples, CRT loss diagnosis module 502 may apportion CRT loss to more, fewer, or different reasons for CRT loss. Furthermore, CRT loss diagnosis module 502 may address the illustrated reasons in an order different than that illustrated in FIG. 7.

In some examples, after apportioning CRT loss to the predetermined reasons for CRT loss (700-710), CRT loss diagnosis module 502 determines whether there is unapportioned CRT loss, e.g., whether the sum of the CRT loss portions for the various predetermined reasons (AT/AF, PVCs, VSEs) does not equal total CRT loss (100%) (712). If there is unapportioned CRT loss ("Y" branch of 712), the remaining CRT loss may be apportioned to an "other" category of reasons for CRT loss (714). Other reasons for CRT loss may that may not be captured by the predetermined reasons of AT/AF, PVCs, VSEs may include, as examples, NSTs, premature atrial contractions that are too fast for IMD 106 to track according to a programmed detection criterion, premature ventricular contractions that are too slow for IMD 106 to identify according to a programmed detection criterion, treated VSEs, or atrial undersensing.

Figure 8:
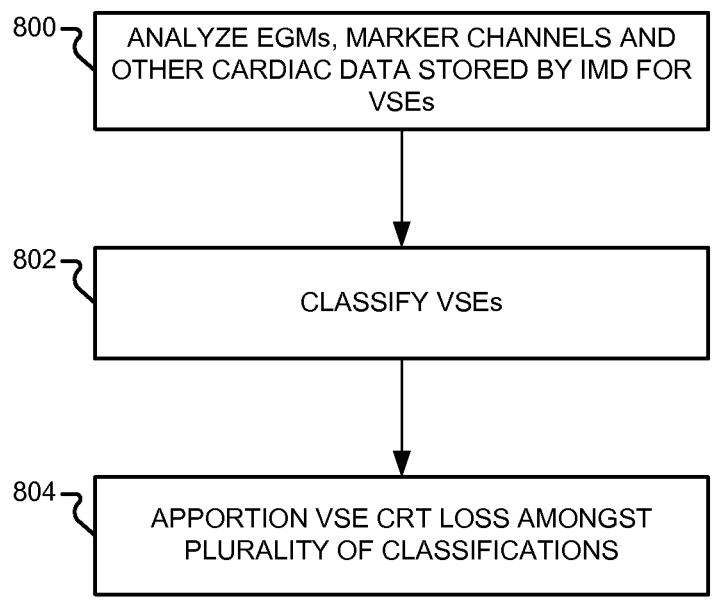
FIG. 8 is a flow diagram illustrating an example method that includes classifying ventricular sense episodes (VSEs) diagnosed by an IMD and apportioning CRT loss amongst a plurality of VSE classifications.

FIG. 8 is a flow diagram illustrating an example method that includes classifying VSEs diagnosed by an IMD and apportioning CRT loss amongst a plurality of VSE classifications. In some examples, instead of, or in addition to, apportioning a portion of the CRT loss to VSEs as a single category, CRT loss diagnosis module 502 may apportion CRT loss amongst a plurality of predetermined VSE classifications based on the occurrence and duration of VSEs meeting such classifications.

According to the example method, episode classification module 504 analyzes the EGMs, marker channels, other cardiac data, or any other IMD data stored by IMD 106 for VSEs detected by the IMD since the last data download (800). Episode classification module 504 classifies each of the VSEs as being one of a plurality of predetermined classifications based on the analysis (802). CRT loss diagnosis module 502 apportions the CRT loss attributable to VSEs generally amongst the plurality of classifications based on the numbers and durations of the VSEs within each of the classifications as determined by the episode classification module 504 (804).

Figure 9:
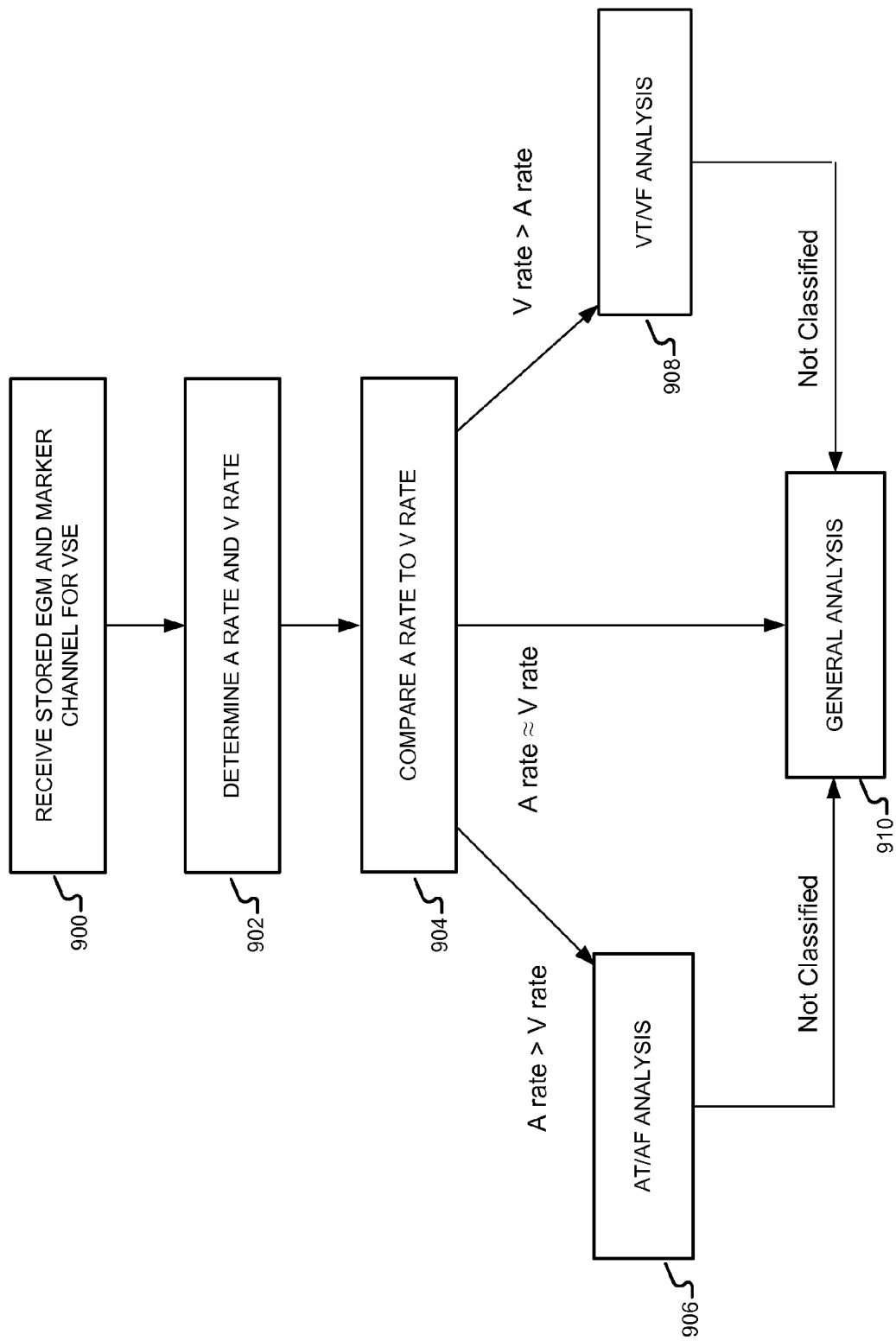
FIG. 9 is a flow diagram illustrating an example method for determining how to classify VSEs based on a comparison of a ventricular rate during the VSE to an atrial rate during the VSE.

FIG. 9 is a flow diagram illustrating an example method for determining how to classify a VSE based on a comparison of a ventricular rate during the VSE to an atrial rate during the VSE. According to the example of FIG. 9, episode classification module 504 receives the stored EGM and marker channel data for the VSE, e.g., from IMD 106 or data store 304 (900). Episode classification module 504 may determine an atrial rate and ventricular rate for the VSE based on one or both of the EGM or marker channel using any known technique (902).

Episode classification module 504 may then compare the atrial rate determined for the VSE to the ventricular rate determined for the VSE (904). If the atrial rate is greater than, e.g., adequately greater than, the ventricular rate, episode classification module 504 implements an AT/AF analysis to classify the VSE (906). In some examples, episode classification module 504 additionally or alternatively implements an AT/AF analysis to classify the VSE (906) when the cardiac data from IMD 106 indicates that the IMD detected AT/AF during the VSE. If the ventricular rate is greater than, e.g., adequately greater than, the atrial rate, episode classification module 504 implements a VT/VF analysis to classify the VSE (908). If the atrial and ventricular rates are approximately equal or equal, episode classification module 504 implements a general analysis to classify the VSE (910). Furthermore, as illustrated by FIG. 9, episode classification module 504 may implement the general analysis (910) to classify VSEs that were analyzed with the AT/AF analysis (906) or VT/VF analysis (908) based on the comparison of ventricular and atrial rates (904), but that were not able to be classified based on those analyses, e.g., due to failure to meet one or more criteria for classification according to those analyses.

In some examples, the EGM and marker channel data analyzed by episode classification module 504 for each of the VSEs includes the latest occurring run of ten or more ventricular sensed events, e.g., intrinsic depolarizations, without intervening ventricular paced events, stored by the IMD for the VSE. If there is no such run of ventricular sensed events, but the marker channel stored by the IMD for the VSE ends with a run of five or more ventricular sensed events, then that run is taken as the VSE. If neither of these situations is true, then the VSE is taken to be the longest run of ventricular sensed events during the VSE, using the later occurring run in the event of a tie. In any case, the start of the VSE is the marker for the first ventricular sensed event in the run, and the end of the VSE is the marker for the last ventricular sensed event in the run. Those two markers and any markers in between are considered to be "within" the VSE.

The atrial and ventricular rates compared according to the example method of FIG. 9 may be an average, mean, median or mode of atrial and ventricular rates. In one example, episode classification module 504 determines an average ventricular rate during the VSE by first examining the set of V-V intervals immediately preceding each of the ventricular events within the VSE. The lowest two and highest two V-V intervals are removed, and episode classification module 504 determines the average V-V interval as the interval that falls at (or just below) the 75$^{th}$ percentile of interval length from this set. Rather than the mean or median, the 75$^{th}$ percentile is used to give consistency to cases of bigemeny or alternating short-long V-V intervals. The average ventricular rate during the VSE may then be calculated for the average V-V interval. Episode classification module 504 may calculate the average atrial rate during the VSE in an analogous way, using the atrial events within the VSE.

Figure 10:
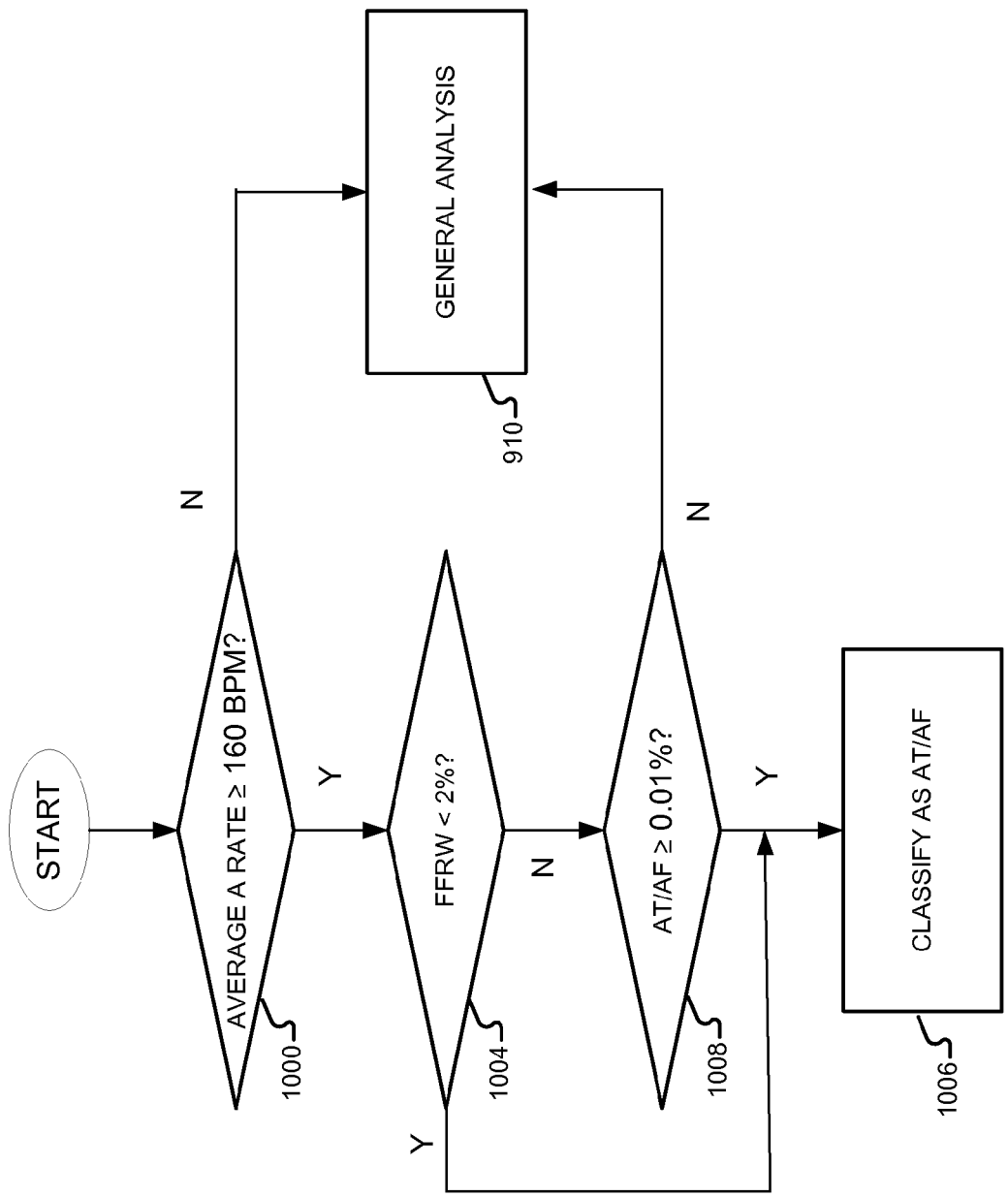
FIG. 10 is a flow diagram illustrating an example method for classifying VSEs during which an atrial rate is greater than a ventricular rate.

FIG. 10 is a flow diagram illustrating an example method for classifying VSEs during which an atrial rate is greater than a ventricular rate. The example method of FIG. 10 may correspond to the AT/AF analysis of FIG. 9 (906).

According to the example method of FIG. 10, episode classification module 504 determines whether the average atrial rate, e.g., determined as described above with respect to FIG. 9, is greater than a threshold atrial rate, which in this case is 160 beats-per-minute (BPM) (1000). If the average atrial rate does not exceed or equal this threshold ("N" branch of 1000), episode classification module 504 does not classify the VSE as AT/AF, e.g., as being due to conducted AT/AF, and instead analyzes the VSE according to the general analysis described in greater detail below with respect to FIG. 12 (910). If the average atrial rate does exceed or equal this threshold ("Y" branch of 1000), episode classification module 504 proceeds to determine whether relatively high average atrial rate is most likely due to true AT/AF.

For example, episode classification module 504 may determine whether far-field R-waves (FFRWs) occurred infrequently, e.g., less than a threshold percent of time, since the latest download from IMD 106 (1004). In the illustrated example, the threshold percentage of time is 2%. FFRWs are R-waves inappropriately detected within an atrial channel, which may cause the average atrial rate determined by episode classification module 504 based on the marker channel for a VSE to be inappropriately high. If FFRWs are adequately infrequent ("Y" of 1004), episode classification module 504 classifies the VSE as AT/AF.

If FFRWs are not adequately infrequent ("N" of 1004), episode classification module 504 determines whether the sensed cardiac data from IMD 106 indicates that AT/AF was sufficiently prevalent since the last download from IMD 106 to believe that the high atrial rate VSE is due to AT/AF despite the relatively prevalent FFRWs (1008). In the illustrated example, if episode classification module 504 determines that the data from IMD 106 indicates that AT/AF occurred greater than or equal to 0.01% of the time since the last download ("Y" branch of 1008), episode classification module 504 classifies the VSE as AT/AF. If episode classification module 504 determines that the data from IMD 106 indicates that AT/AF occurred less than 0.01% of the time since the last download ("N" branch of 1008), episode classification module 504 applies a general analysis, such as that discussed in greater detail with respect to FIG. 12, to classify the VSE (910).

Figure 11:
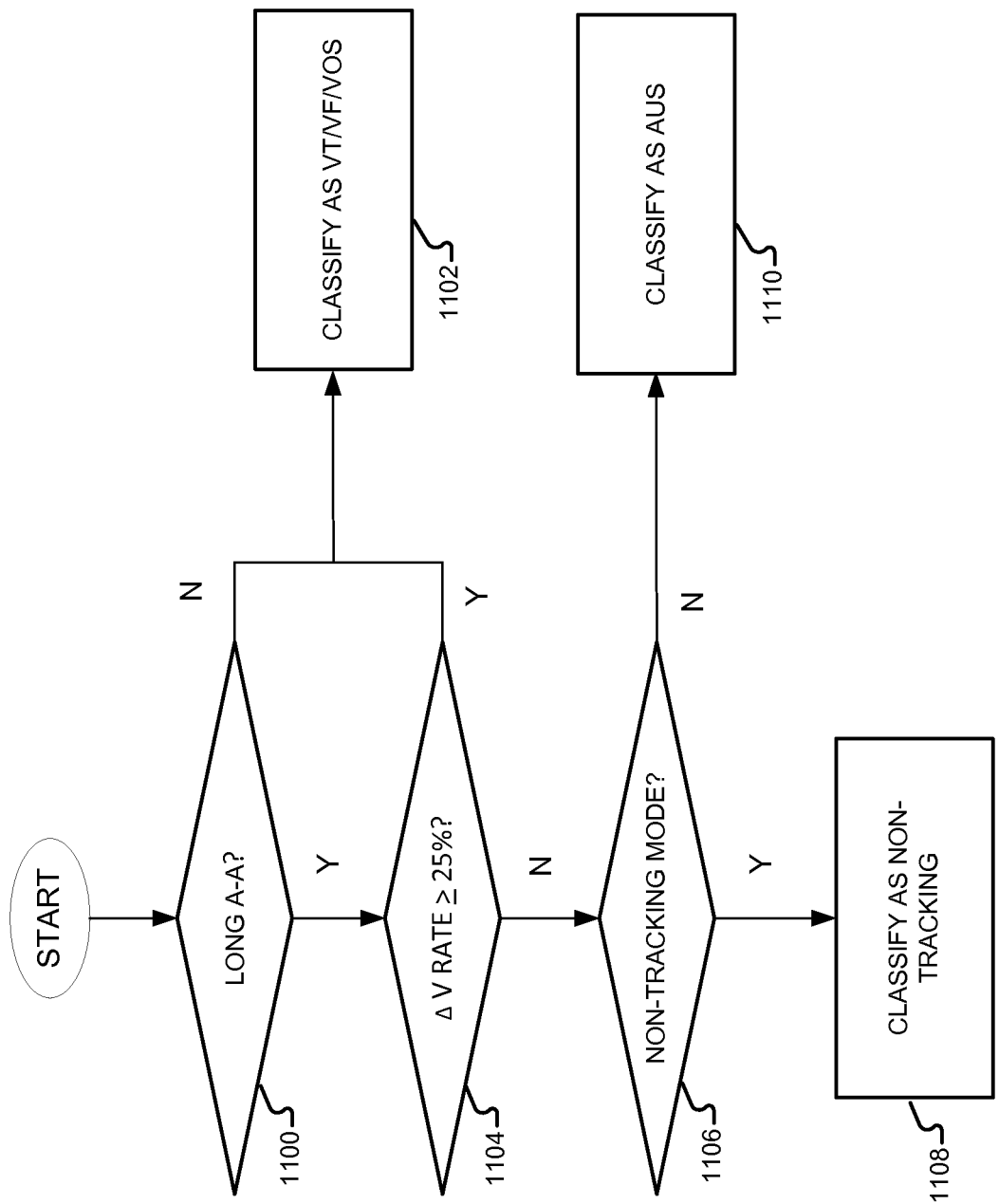
FIG. 11 is a flow diagram illustrating an example method for classifying VSEs during which a ventricular rate is greater than an atrial rate.

FIG. 11 is a flow diagram illustrating an example method for classifying VSEs during which a ventricular rate is greater than an atrial rate. The example method of FIG. 11 may correspond to the VT/VF analysis of FIG. 9 (908).

According to the example method of FIG. 11, episode classification module 504 determines whether a long A-A interval is present within the VSE (1100). A long A-A interval may be an A-A interval greater (longer) than a threshold duration, such as 1500 milliseconds (ms). Episode classification module 504 may also determine that a long A-A interval occurred if there are no atrial events in between the start and the end of the VSE. If there is no long A-A interval ("N" branch of 1100), episode classification module 504 classifies the VSE as VT/VF/VOS, e.g., as being one of VT, VF, or due to ventricular oversensing (VOS) (1102).

If there is a long A-A interval ("Y" branch of 1100), episode classification module 504 determines whether a change in the ventricular rate during the VSE is sufficient such that, despite the long A-A interval, the VSE may be classified as VT/VF/VOS. In particular, episode classification module 504 determines whether a change, e.g., percentage, in ventricular rate during the VSE is greater than threshold value, e.g., 25% (1104). If the change in ventricular rate is greater than or equal to the threshold ("Y" branch of 1104), episode classification module 504 classifies the VSE as VT/VF/VOS (1102).

The change in ventricular rate may be a percentage change in ventricular rate. To calculate the percentage change in ventricular rate, episode classification module 504 may determine the pre-VSE average V-V interval, and the average V-V interval during the VSE. The average V-V intervals may be determined as described above with reference to FIG. 9, or may be determined by removing the shortest two V-V intervals and the longest two V-V intervals of either group (pre-VSE or VSE), and taking the mean of the remaining V-V intervals. Episode classification module 504 may determine the percent change in ventricular rate by determining the difference between the pre-VSE and VSE averages, and dividing the difference by the pre-VSE average V-V interval.

If the change in ventricular rate is less than the threshold ("N" branch of 1104), episode classification module 504 determines, based on data from IMD 106, whether the IMD was in a non-tracking pacing mode, e.g., VVI or DDI, during the VSE (1106). If IMD 106 was in a non-tracking mode ("Y" branch of 1106), episode classification module 504 classifies the VSE as NON-TRACKING (1108). NON-TRACKING is an example of a classification of a VSE according to pacing mode. If IMD 106 was in a tracking mode ("N" branch of 1106), episode classification module 504 classifies the VSE as ATRIAL UNDERSENSING (AUS) (1110).

In the example illustrated by FIG. 11, all VSEs analyzed according to the VT/VF analysis (908) are classified as one of: (1) VT/VF/VOS; (2) AUS; or (3) NON-TRACKING. In other examples, some VSEs analyzed according to the VT/VF analysis (908) are not classified by the VT/VF analysis, and proceed to analysis according to the general analysis (910). For example, rather than determine whether the IMD was in a non-tracking pacing mode (1106) for a VSE with a long A-A interval ("Y" branch of 1100) and a change in ventricular rate less than 25% ("N" branch of 1104), as illustrated in FIG. 11, episode classification module 504 may instead proceed to analyze the VSE according to the general analysis, e.g., such as that illustrated with respect to FIG. 12.

Figure 12:
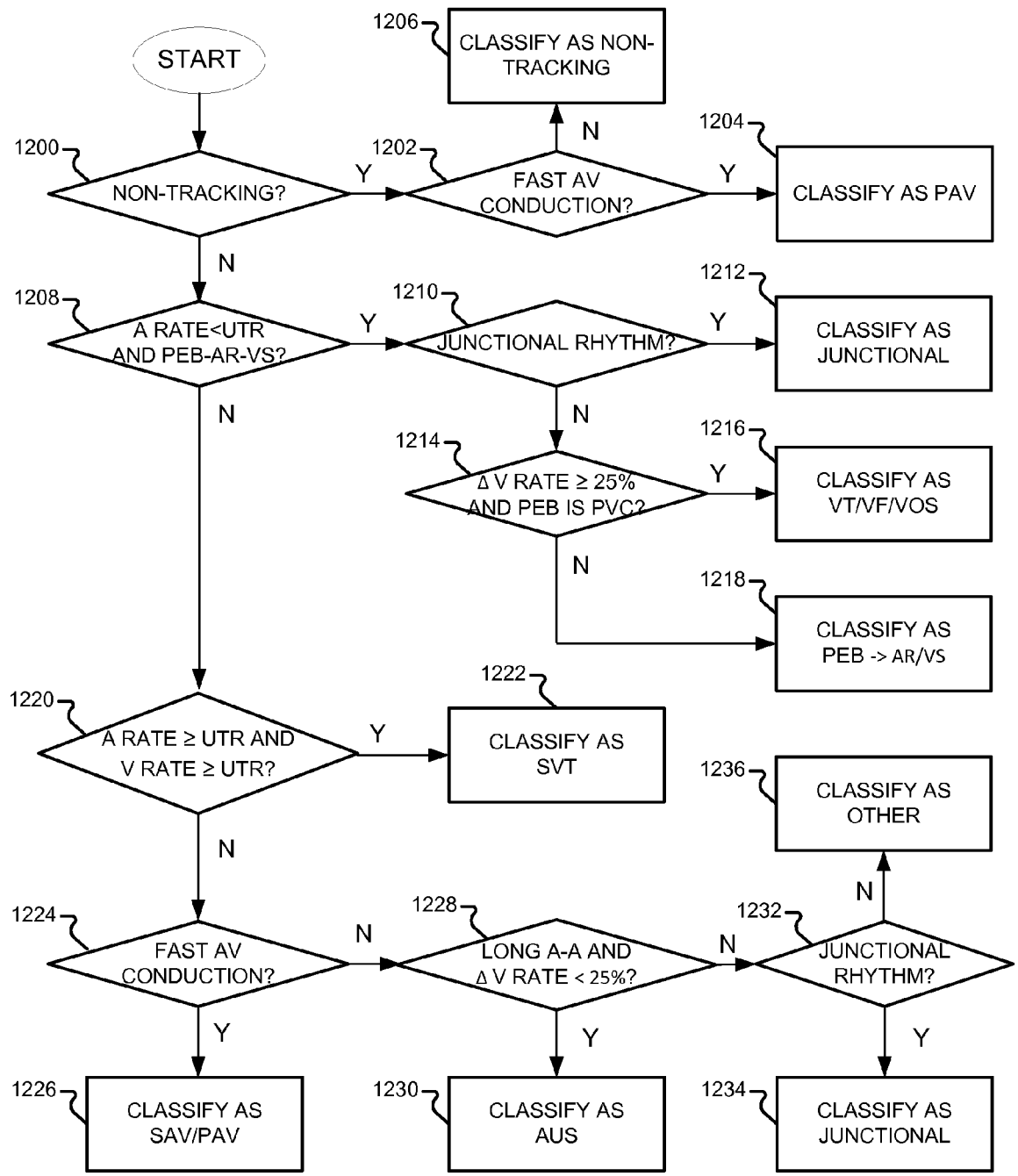
FIG. 12 is a flow diagram illustrating another example method for classifying VSEs.

FIG. 12 is a flow diagram illustrating an example method for classifying VSEs during which a ventricular rate is equal to or approximately equal to an atrial rate, or which were not able to be classified by the AT/AF or VT/VF analyses discussed above with respect to FIGS. 10 and 11. The example method of FIG. 12 may correspond to the general analysis of FIG. 9 (910).

According to the example method of FIG. 12, episode classification module 504 determines whether IMD 106 was in a non-tracking mode during the VSE (1200). If IMD 106 was in a non-tracking mode ("Y" branch of 1200), episode classification module 504 determines whether the VSE had fast AV conduction (1202). A VSE may be considered to have fast AV conduction if there are at least five ventricular sensed events within the VSE for which the A-V interval preceding the ventricular sensed event is greater than 90 ms but less than the programmed PAV value, and the previous atrial event is a paced atrial event.

If the VSE has fast AV conduction ("Y" branch of 1202), episode classification module 504 classifies the VSE as PAV (1204). A classification of PAV may indicate that any CRT loss during the PSE classified as PAV may be due to the PAV being programmed too long to facilitate CRT pacing during the VSE. If the VSE does not have fast AV conduction ("N" branch of 1202), episode classification module 504 classifies the VSE as NON-TRACKING (1206). A classification of NON-TRACKING may indicate that any CRT loss during the PSE classified as NON-TRACKING may be due to the non-tracking pacing mode not facilitating delivery of CRT by IMD 106 during relatively high atrial rates.

If IMD 106 was in a tracking mode ("N" branch of 1200), episode classification module 504 determines whether there was both an atrial rate during the VSE less than an upper tracking rate (UTR) programmed for the IMD during the VSE, and a PEB-AR-VS pattern during the VSE (1208). A PEB-AR-VS pattern means that a premature ectopic beat (PEB), such as a PVC or a premature atrial contraction (PAC), occurs at the onset of a looping pattern of AR (atrial refractory) and VS (intrinsic ventricular sense) events. This requires a run of five markers that are either an atrial refractory sense (AR) or an atrial sense during the blanking period (Ab), i.e., no atrial paced events, nor atrial sensed events outside of the blanking or refractory periods. The first of the five events must be one of the first five markers within the VSE.

If such a run of AR and/or Ab markers exist, then the event immediately preceding the first AR/Ab will be considered a potential PVC. The run corresponds with a PVC-AR-VS pattern if the following is true: (1) the V-V preceding that potential PVC is less than 80% of the average V-V for the two ventricular events before it; and (2) the event immediately before the potential PVC is an atrial event with a preceding A-A interval that is not more than 20 ms shorter than the V-V interval of the potential PVC. If the AR/Ab run is not a PVC-AR-VS pattern, then it can be an PAC-AR-VS pattern if the following is true: (1) the event immediately preceding the potential PVC is either an AR or an Ab; and (2) The A-A preceding that potential PAC is less than 80% of the average A-A for the two atrial events before it. If neither a PVC-AR-VS pattern nor a PAC-AR-VS pattern is detected, then this run of AR/Ab events is not considered to be a PEB-AR-VS pattern.

If episode classification module 504 determines that there was both an atrial rate less than the UTR and a PEB-AR-VS pattern during the VSE ("Y" branch of 1208), episode classification module 504 determines whether there was a junctional rhythm during the VSE (1210). A VSE may be considered to have junctional rhythm if there are at least five events within the VSE that signify a junctional beat. A junctional beat may be defined as: (1) a ventricular sensed event whose preceding A-V interval is less than or equal to 70 ms, and where the previous most recent atrial event is not a paced atrial event; or (2) an atrial sensed event, an AR, or an Ab whose preceding V-A interval is less than or equal to 70 ms, and where the previous most recent ventricular event that is not a ventricular refractory sense (VR) is a sensed ventricular event. Additionally, in order for a VSE to be considered to have junctional rhythm, it may be required that there be more junctional beats than non junctional beats within the VSE. A non junctional beat may be defined as any of the following: (1) a ventricular paced event that is not a ventricular sense response (VSR) pace; (2) a ventricular sensed event that is not a junctional beat nor followed by an atrial event that is considered a junctional beat due to having a V-A interval of 70 ms or less from this ventricular event; (3) an atrial sensed event, an AR, or an Ab that is not a junctional beat, nor followed by a ventricular event that is considered a junctional beat due to having an A-V interval of 70 ms or less from this atrial event. A VSR pace is a resynchronization pace delivered during a premature beat. More particularly, if an IMD senses activation of a ventricle before pacing was to be delivered, the IMD may rapidly deliver a responsive VSR pacing pulse to the opposite ventricle. A regular paced beat is not a junctional beat, whereas a VSR beat may be in response to junctional beat.

If episode classification module 504 determines that there was a junctional rhythm during the VSE ("Y" branch of 1210), episode classification module 504 classifies the VSE as JUNCTIONAL (1212). If episode classification module 504 determines that there was not a junctional rhythm during the VSE ("N" branch of 1210), episode classification module 504 determines whether there was a change in ventricular rate greater than or equal to a threshold, e.g., 25%, and the PEB of the PEB-AR-VS cycle is a PVC (1214). If both of these conditions are true ("Y" branch of 1214), episode classification module 504 classifies the VSE as VT/VF/VOS (1216). If either of these conditions is untrue ("N" branch of 1214), episode classification module 504 classifies the VSE as the result of a PEB leading to an AR/VS pattern, i.e., as PEB→AR/VS (1218).

If either the atrial rate was greater than or equal to the UTR or there was not PEB-AR-VS ("N" branch of 1208), episode classification module 504 determines whether there was both an atrial rate and ventricular rate greater than or equal to the UTR (1220). If both conditions were true during the VSE ("Y" branch of 1220), episode classification module 504 classifies the VSE as a supraventricular tachycardia (SVT) (1222). If either condition was not true ("N" branch of 1220), episode classification module 504 determines whether was fast AV condition during the VSE (1224). The VSE may be considered to have fast AV conduction if there are at least five ventricular sensed events within the VSE for which the A-V interval preceding the ventricular sensed event is greater than 70 ms but less than the programmed SAV value, the previous atrial event is not a paced atrial event, and the device is not programmed in a non-tracking pacing mode (i.e. not VVI, VVIR, DDI, or DDIR). If episode classification module 504 determines that there was fast AV condition during the VSE ("Y" branch of 1224), episode classification module 504 classifies the VSE as SAV/PAV (1226). Such a classification may indicate that CRT loss attributable to a VSE so classified may have been caused by one or both of the SAV or PAV intervals being programmed at too long a value.

If episode classification module 504 determines that there was not fast AV condition during the VSE ("N" branch of 1224), episode classification module 504 determines whether the VSE had both a long A-A interval and a change in ventricular rate less than a threshold, e.g., 25% (1228). If both conditions are true ("Y" of 1228), episode classification module 504 classifies the VSE as AUS (1230). If either condition is not true ("N" of 1228), episode classification module 504 determines whether the VSE exhibits a junctional rhythm, e.g., according to the criteria described above (1232). If the VSE exhibits a junctional rhythm ("Y" branch of 1232), episode classification module 504 classifies the VSE as JUNCTIONAL (1234). If the VSE does not exhibit a junctional rhythm ("N" branch of 1232), episode classification module 504 classifies the VSE as OTHER (1236).

Various examples have been described. However, one of ordinary skill in the art will appreciate that various modifications may be made to the described examples. For example, amounts of CRT loss have generally been described as denominations of time, e.g., seconds, minutes, or hours, represented as percentages, e.g., of the total time since the last download from an IMD. In other examples, an amount of CRT loss need not be expressed as a percentage, e.g. CRT loss could be expressed as an absolute value of time CRT was not delivered, like seconds, minutes, or hours CRT was not delivered.

Furthermore, the amount of CRT loss need not be quantified or apportioned based the passage of time, e.g., seconds, minutes, or hours, and instead could be quantified or apportioned based on the number of events. For example, the amount of time CRT loss may be a number of cardiac beats for which CRT was not delivered. Similarly, the amount of beats, rather than seconds, for which AT/AF, PVCs or VSEs were occurring may be used to determine the apportionment of the CRT loss amongst AT/AF, PVCs or VSEs. These and other examples are within the scope of the following claims.

The invention claimed is:

1. A system comprising:
a processor configured to receive data generated by an implantable medical device (IMD) that is configured to deliver cardiac resynchronization therapy (CRT), wherein the received data comprises CRT data and sensed cardiac data, wherein the CRT data indicates an amount of time for which the IMD did not deliver CRT to a patient, and wherein the sensed cardiac data indicates intrinsic cardiac activity of the patient that was sensed by the IMD; and
a CRT loss diagnosis module configured to analyze the CRT data and the sensed cardiac data, and apportion the amount of time amongst a plurality of predetermined reasons for CRT loss based on the analysis.

2. The system of claim 1,
wherein the amount of time comprises a percentage of a period of time, and
wherein the CRT loss diagnosis module is configured to determine a percentage for each of the predetermined reasons.

3. The system of claim 1, wherein the plurality of predetermined reasons for CRT loss comprises at least one of atrial tachyarrhythmia or premature ventricular contractions.

4. The system of claim 3,
wherein the sensed cardiac data received from the IMD indicates an amount of atrial tachyarrhythmia experienced by the patient, and
wherein the CRT loss diagnosis module apportions a portion of the amount of time for which the IMD did not deliver CRT to the patient to the predetermined reason of atrial tachyarrhythmia based on the amount of atrial tachyarrhythmia.

5. The system of claim 3,
wherein the sensed cardiac data received from the IMD indicates an amount of premature ventricular contractions experienced by the patient, and
wherein the CRT loss diagnosis module apportions a portion of the amount of time for which the IMD did not deliver CRT to the patient to the predetermined reason of premature ventricular contractions based on the amount of premature ventricular contractions.

6. The system of claim 3,
wherein the sensed cardiac data comprises data for one or more ventricular sense episodes, the data for each of the ventricular sense episodes including data indicating the occurrence and timing of atrial and ventricular events during the ventricular sense episode,
wherein ventricular sense episodes are tachyarrhythmia episodes detected by an IMD based on intervals between adjacent ventricular events during the episode meeting a tachyarrhythmia criterion, and
wherein the plurality of predetermined reasons for CRT loss comprises ventricular sense episodes.

7. The system of claim 6,
wherein the sensed cardiac data received from the IMD indicates an amount of ventricular sense episodes experienced by the patient, and
wherein the CRT loss diagnosis module apportions a portion of the amount of time for which the IMD did not deliver CRT to the patient to the predetermined reason of ventricular sense episodes based on the amount of ventricular sense episodes.

8. The system of claim 6,
further comprising an episode classification module configured to analyze the sensed cardiac data for the ventricular sense episodes, and classify each of ventricular sense episodes as one of a plurality of predetermined classifications based on the analysis,
wherein the plurality of predetermined reasons for CRT loss comprises at least some of the predetermined classifications, and
wherein the CRT loss diagnosis module is configured to apportion at least some the amount of time to the predetermined classifications as reasons for CRT loss based on the classifications of the ventricular sense episodes by the episode classification module.

9. The system of claim 8, wherein the predetermined classifications comprise at least one of a ventricular tachyarrhythmia classification, a supraventricular classification, or a ventricular oversensing classification.

10. The system of claim 8, wherein the predetermined classifications comprise at least one of a programmed atrioventricular interval length classification, a programmed pacing mode classification, an atrial undersensing classification, an atrial refractory sense to ventricular sense classification, or a junctional rhythm classification.

11. The system of claim 1, further comprising an external computing device configured to present a representation of the apportionment of the amount of time amongst the plurality of predetermined reasons to a user.

12. The system of claim 11, wherein the external computing device is configured to:
analyze the apportionment of the amount of time amongst the plurality of predetermined reasons; and
recommend modification of at least one programmable parameter of the IMD to the user based on the apportionment.

* * * * *